United States Patent
Perlman

(10) Patent No.: US 11,364,085 B2
(45) Date of Patent: Jun. 21, 2022

(54) NO-CONTACT COVER FOR STETHOSCOPES AND OTHER ARTICLES

(71) Applicant: BUNNYCAP, LLC, Bergenfield, NJ (US)

(72) Inventor: Alan Scott Perlman, Bergenfield, NJ (US)

(73) Assignee: BUNNYCAP, LLC, Bergenfield, NJ (US)

( * ) Notice: Subject to any disclaimer, the term of this patent is extended or adjusted under 35 U.S.C. 154(b) by 132 days.

(21) Appl. No.: 16/670,590

(22) Filed: Oct. 31, 2019

(65) Prior Publication Data
US 2020/0138538 A1 May 7, 2020

Related U.S. Application Data

(60) Provisional application No. 62/755,031, filed on Nov. 2, 2018.

(51) Int. Cl.
*A61B 50/30* (2016.01)
*A61B 7/02* (2006.01)

(52) U.S. Cl.
CPC ............... *A61B 50/30* (2016.02); *A61B 7/02* (2013.01)

(58) Field of Classification Search
CPC .... B65D 83/08; B65D 83/00; B65D 83/0894; A61B 46/10; A61B 50/20; A61B 50/30; A61B 7/02; B65H 18/00; B65H 18/10; B65H 18/145; B65H 35/006; B65H 37/002; B65H 3/00; B65B 67/04; B65B 47/14; B65B 67/1266

USPC .................................. 422/28, 300; 221/9, 40
See application file for complete search history.

(56) References Cited

U.S. PATENT DOCUMENTS

| | | | |
|---|---|---|---|
| 3,162,301 A * | 12/1964 | Cage, Jr. ................... | A61J 7/04 206/534 |
| 3,365,099 A * | 1/1968 | Mctaggart ................. | A61J 7/04 206/499 |
| 3,747,298 A * | 7/1973 | Lieberman .......... | B65B 67/1266 53/384.1 |

(Continued)

FOREIGN PATENT DOCUMENTS

WO      2011097418 A2     8/2011
WO      2015175456 A1     11/2015

*Primary Examiner* — Rakesh Kumar
(74) *Attorney, Agent, or Firm* — McNees Wallace & Nurick LLC

(57) ABSTRACT

A system for dispensing sterile covers for a stethoscope or other medical device, including a container including elongated members positioned in the container, terminating at tips proximate one end of the container; one or more collapsed pouches positioned inside the container, each pouch having open and closed ends and retainers, each retainer adapted to receive a corresponding elongated member, the collapsed pouches being supported on the elongated members; each pouch comprising a tab positioned proximate the open end for being grasped and pulled in a direction away and downwards from the elongated members, the open end forming an open position defined by the retainers and the tab for receiving a head of the stethoscope inside the pouch while the retainers remain engaged with the elongated members; after use, the pouch is removable from the stethoscope without a user contacting a patient contacting region of the cover.

7 Claims, 23 Drawing Sheets

(56) References Cited

U.S. PATENT DOCUMENTS

| | | | |
|---|---|---|---|
| 5,000,344 A * | 3/1991 | Janssen | A47F 1/08 221/92 |
| 5,511,689 A * | 4/1996 | Frank | A61F 15/002 206/440 |
| 5,564,431 A | 10/1996 | Seward | |
| 5,975,083 A * | 11/1999 | Henderson, Jr. | A41D 13/082 128/878 |
| 6,018,835 A * | 2/2000 | Schonfeld | B08B 3/02 15/97.1 |
| 6,643,998 B1 * | 11/2003 | Curtis | B65B 9/13 53/434 |
| 7,086,563 B2 * | 8/2006 | Maffei | A61F 15/001 221/305 |
| 7,117,971 B1 * | 10/2006 | Cornacchia | A61B 7/02 221/266 |
| 7,866,507 B2 * | 1/2011 | Sawin | B65D 25/205 222/1 |
| 7,891,462 B2 | 2/2011 | Hmayakyan et al. | |
| 8,479,956 B2 * | 7/2013 | Lewis, II | A47K 5/1202 222/153.03 |
| 8,662,244 B2 | 3/2014 | Fishberger et al. | |
| 9,220,565 B2 | 12/2015 | Perlman | |
| 9,486,287 B2 * | 11/2016 | Beebe | A61B 50/30 |
| 9,675,721 B2 * | 6/2017 | Dayton | A61L 2/24 |
| 9,770,307 B2 | 9/2017 | Krupnick | |
| 9,986,965 B2 * | 6/2018 | Fishberger | A61B 7/02 |
| 2002/0170771 A1 * | 11/2002 | Milam | A61B 7/02 181/131 |
| 2006/0186131 A1 * | 8/2006 | Panning | A47K 10/16 221/63 |
| 2006/0201960 A1 * | 9/2006 | Frayne | B65D 81/052 221/45 |
| 2008/0061073 A1 * | 3/2008 | Laroche | A47K 10/421 221/63 |
| 2008/0222929 A1 * | 9/2008 | Sawin | A47K 10/421 221/45 |
| 2008/0223868 A1 * | 9/2008 | Sawin | B65D 25/205 221/63 |
| 2010/0212995 A1 * | 8/2010 | Hmayakyan | A61B 7/02 181/131 |
| 2011/0101029 A1 * | 5/2011 | Lewis, II | A47K 5/1202 222/325 |
| 2011/0186590 A1 * | 8/2011 | Lee | A61B 50/30 600/528 |
| 2012/0051969 A1 * | 3/2012 | Nahman | A61B 7/02 422/28 |
| 2012/0261593 A1 * | 10/2012 | Noori | A61L 2/10 250/492.1 |
| 2013/0108507 A1 * | 5/2013 | Reiseneder | A61B 46/10 422/28 |
| 2013/0270288 A1 * | 10/2013 | Xu | A43B 3/106 221/1 |
| 2014/0124287 A1 * | 5/2014 | Fishberger | A61B 7/02 181/131 |
| 2015/0128997 A1 * | 5/2015 | Lesic | A61B 7/00 15/210.1 |
| 2015/0136896 A1 * | 5/2015 | Beebe | H05K 5/03 428/80 |
| 2015/0327933 A1 * | 11/2015 | Perlman | A61B 50/30 181/131 |
| 2015/0360897 A1 * | 12/2015 | Bekavac | B65D 33/002 312/35 |
| 2016/0045266 A1 | 2/2016 | Deporto et al. | |
| 2017/0049954 A1 * | 2/2017 | Edwards | A61M 5/3202 |
| 2017/0095224 A1 | 4/2017 | Olgun | |
| 2017/0258435 A1 * | 9/2017 | Fishberger | A61B 7/02 |
| 2018/0201433 A1 * | 7/2018 | Mader | B65D 83/08 |
| 2018/0221103 A1 * | 8/2018 | Bayasi | A61B 7/02 |
| 2019/0218018 A1 * | 7/2019 | Umentum | B65D 83/0805 |
| 2020/0138538 A1 * | 5/2020 | Perlman | A61B 50/30 |
| 2020/0138539 A1 * | 5/2020 | Perlman | A61B 50/30 |

\* cited by examiner

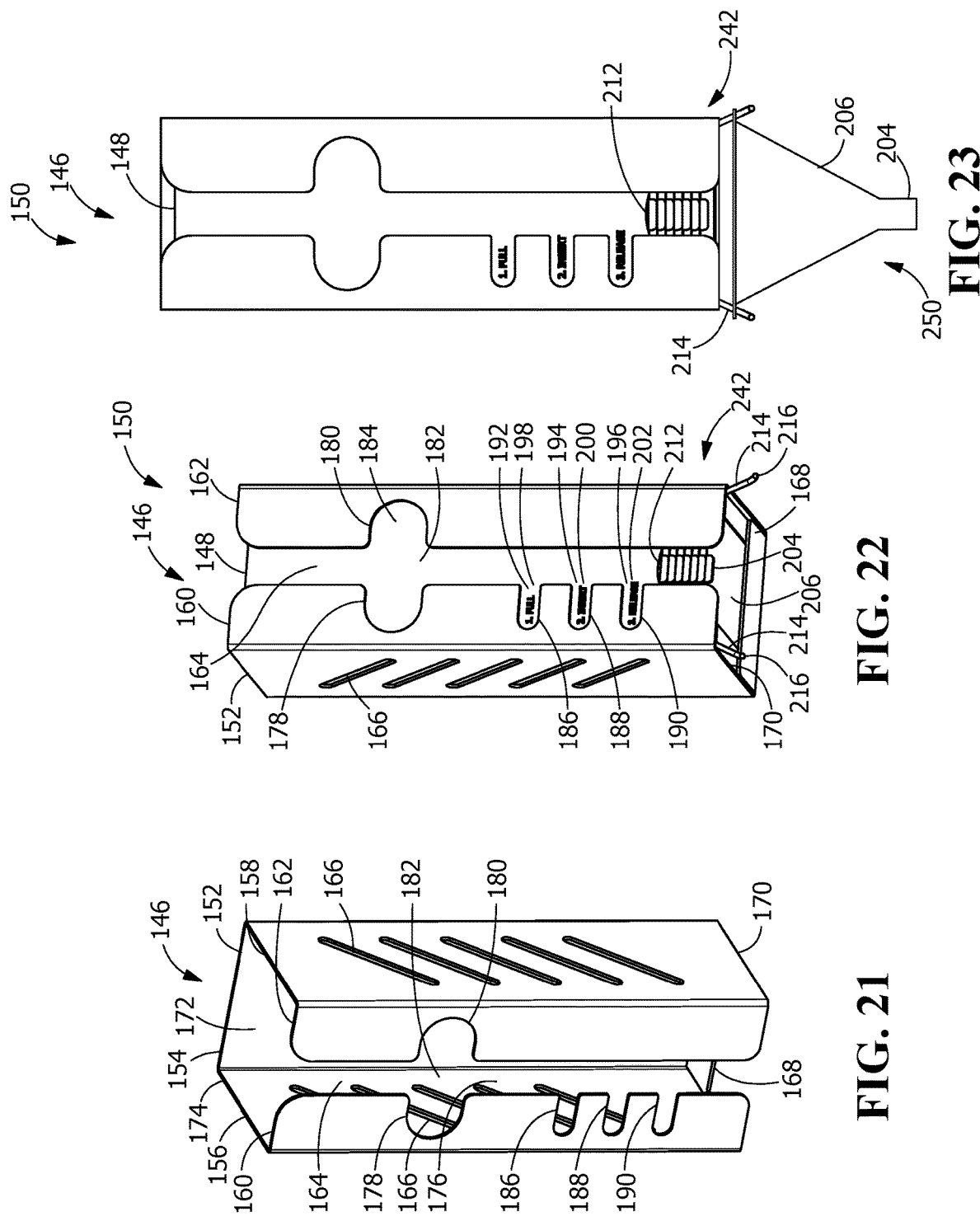

NO-CONTACT COVER FOR STETHOSCOPES AND OTHER ARTICLES

BACKGROUND

The transmission of micro-organisms between patients in health care settings remains a major health problem and accounts for significant morbidity and mortality. Based upon considerable evidence, it is accepted that contaminated hands of health care workers are a major route of cross-infection amongst patients. Despite this recognized risk for transmission and the subsequent incorporation by medical facilities of hand hygiene practices, the rate of transmission of hospital-acquired organisms has not declined appreciably in recent years. There is increasing evidence that stethoscopes are a major vector for the patient-patient transmission of infectious organisms.

One strategy for addressing potential bacterial contamination of the stethoscope head is the one-use disposable stethoscope. This approach, while somewhat effective, is expensive. Disposable stethoscopes are also of inferior acoustic quality than standard stethoscopes.

Another strategy is to disinfect the stethoscope head using alcohol pads or hand cleanser. However, several studies have indicated that although this is an effective means of reducing bacterial colony counts on the diaphragm and bell of stethoscopes, a 2007 review of the subject revealed that 45-68% of physicians and nurses surveyed reported "never" or "rarely" cleaning their stethoscopes. Another survey reported that only 24% of respondents disinfected their stethoscopes after every use.

There is a need in the art for a convenient and inexpensive system or method that reduces the patient-patient transmission of infectious organisms.

SUMMARY OF THE INVENTION

In one embodiment, a system for dispensing sterile covers for a stethoscope or other medical device, includes a container including at least two elongated members positioned in the container and terminating at tips proximate one end of the container. The system further includes one or more collapsed pouches positioned inside the container, each pouch having an open end and a closed end and a support structure positioned proximate the open end, the support structure having a pair of first retainers, each first retainer adapted to receive a corresponding elongated member of the at least two elongated members, the one or more collapsed pouches being supported on the elongated members. The system further includes each pouch including a first tab positioned proximate the open end, the first tab being arranged and disposed such that in response to the first tab of a corresponding pouch positioned nearest the tips of the at least two elongated members being grasped and pulled in a direction downwards and away from the at least two elongated members, the open end forming a first open position defined by the pair of first retainers and the first tab for receiving a head of the stethoscope or other medical device inside the pouch while the first retainers remain engaged with the at least two elongated members.

In one aspect, the system includes a second tab positioned proximate the open end opposite the first tab; the first tab and the second tab being arranged and disposed such that in response to the second tab being grasped and pulled in a direction away from the stethoscope or other medical device received inside the pouch or the second tab being pulled in a direction away from the first tab, the open end forming a second open position permitting removal of the stethoscope or other medical device from the pouch.

In another aspect, the system includes support structure including separate support structure portions, each support structure portion having a corresponding first retainer.

In a further aspect, the system includes the two elongated members arranged non-parallel to one another.

In yet another aspect, the system includes the tips of the elongated members extending exterior of the container.

In one aspect, the system includes the container including a removable lid at the one end to expose the plurality of collapsed pouches for removal from the container.

In another aspect, the system further comprises a dispenser adapted to receive the container.

In a further aspect, the system includes the two elongated members connected to one another.

In yet another aspect, the system includes the tips including second retainers.

In one aspect, the system includes the open end including elastic material.

In a further aspect, the system includes the second open position including an opened weakened region extending to the open end proximate the second tab.

In yet another aspect, the system includes the weakened region including a perforation, a slit, a reinforced slit or a combination thereof.

In one aspect, the system includes a third tab positioned proximate the closed end.

In another aspect, the system includes the container including slots for permitting viewing of container indicia.

In yet another aspect, the system includes the container indicia including product description information and product installation steps.

In one embodiment, a method for covering a stethoscope or other medical device, includes: providing a container including at least two elongated members positioned in the container and terminating at tips proximate one end of the container, one or more collapsed pouches positioned inside the container, each pouch having an open end and a closed end and a support structure positioned proximate the open end, the support structure having a pair of first retainers, each first retainer adapted to receive a corresponding elongated member of the at least two elongated members. The method further includes the one or more collapsed pouches being supported on the elongated members, each pouch comprising a first tab positioned proximate the open end. The method further includes grasping and pulling the first tab of a corresponding pouch positioned nearest the tips of the at least two elongated members in a direction away from the at least two elongated members, the open end forming a first open position defined by the pair of first retainers and the first tab for receiving a head of the stethoscope or other medical device inside the pouch while the first retainers remain engaged with the at least two elongated members. The method further includes orienting the head of the stethoscope or other medical device prior to, simultaneously with, or subsequent to inserting the stethoscope or other medical device inside the pouch.

In another embodiment, a cover for a stethoscope includes a hollow flexible or non-flexible body having an opening for surroundingly receiving a stethoscope head therein, and a protrusion positioned opposite the opening, the protrusion extending sufficiently outwardly from a surface of the body for permitting the protrusion to be grasped by a user. The cover further includes in response to the protrusion being grasped by the user and application of a separation force to the protrusion and the body by the user, the separation force separating the body from the stethoscope head without the user contacting the stethoscope head.

In a further embodiment, a dispenser for covering a stethoscope head, the dispenser including an enclosure having an opening for receiving a stethoscope head therein. The dispenser further including a stethoscope cover positioned inside the enclosure and overlapping the opening, the stethoscope cover secured to a carrier. The dispenser further including in response to sufficient insertion of the stethoscope head through the opening and inside the enclosure in contact with the stethoscope head, the stethoscope head being separated from the carrier, and the stethoscope cover surroundingly covering the stethoscope head.

In yet a further embodiment, a method of covering and uncovering a stethoscope head includes securing a hollow flexible or non-flexible body having an opening to a carrier, and sufficiently inserting, such as by a user, a stethoscope head inside the hollow flexible body through the opening to separate the body from the carrier, the body surroundingly receiving the stethoscope head therein, the body including a protrusion extending outwardly from a surface of the body. The method further includes manually grasping the protrusion by the user and applying a separation force in a first direction by the user to the protrusion to separate the body from the stethoscope head without the user contacting the stethoscope head.

In one aspect, the method includes the protrusion positioned opposite the opening.

In another aspect, the method includes, subsequent to orienting the head of the stethoscope or other medical device, removing the pouch containing the inserted stethoscope or other medical device from the container, monitoring a medical condition of a patient with the covered stethoscope head or other medical device, a patient contacting region of the pouch contacting the patient, and removing the cover from the covered stethoscope head or other medical device without a user contacting the patient contacting region of the cover.

In a further aspect, the application of the cover to the head can be manual or electric.

In one aspect, an electronic triggering mechanism may be utilized.

Other features and advantages of the present invention will be apparent from the following more detailed description, taken in conjunction with the accompanying drawings which illustrate, by way of example, the principles of the invention.

BRIEF DESCRIPTION OF THE DRAWINGS

FIG. 21 is an oblique perspective view of an exemplary dispenser receptacle for dispensing covers for covering a stethoscope head.

FIG. 22 is an oblique perspective view of the dispenser receptacle of FIG. 21 securing a container containing covers for covering a stethoscope head.

FIG. 23 is a front view of the dispenser receptacle and container of FIG. 22 with an exemplary cover in an open position for receiving a stethoscope head.

Wherever possible, the same reference numbers will be used throughout the drawings to represent the same parts.

DETAILED DESCRIPTION

Figure 1:
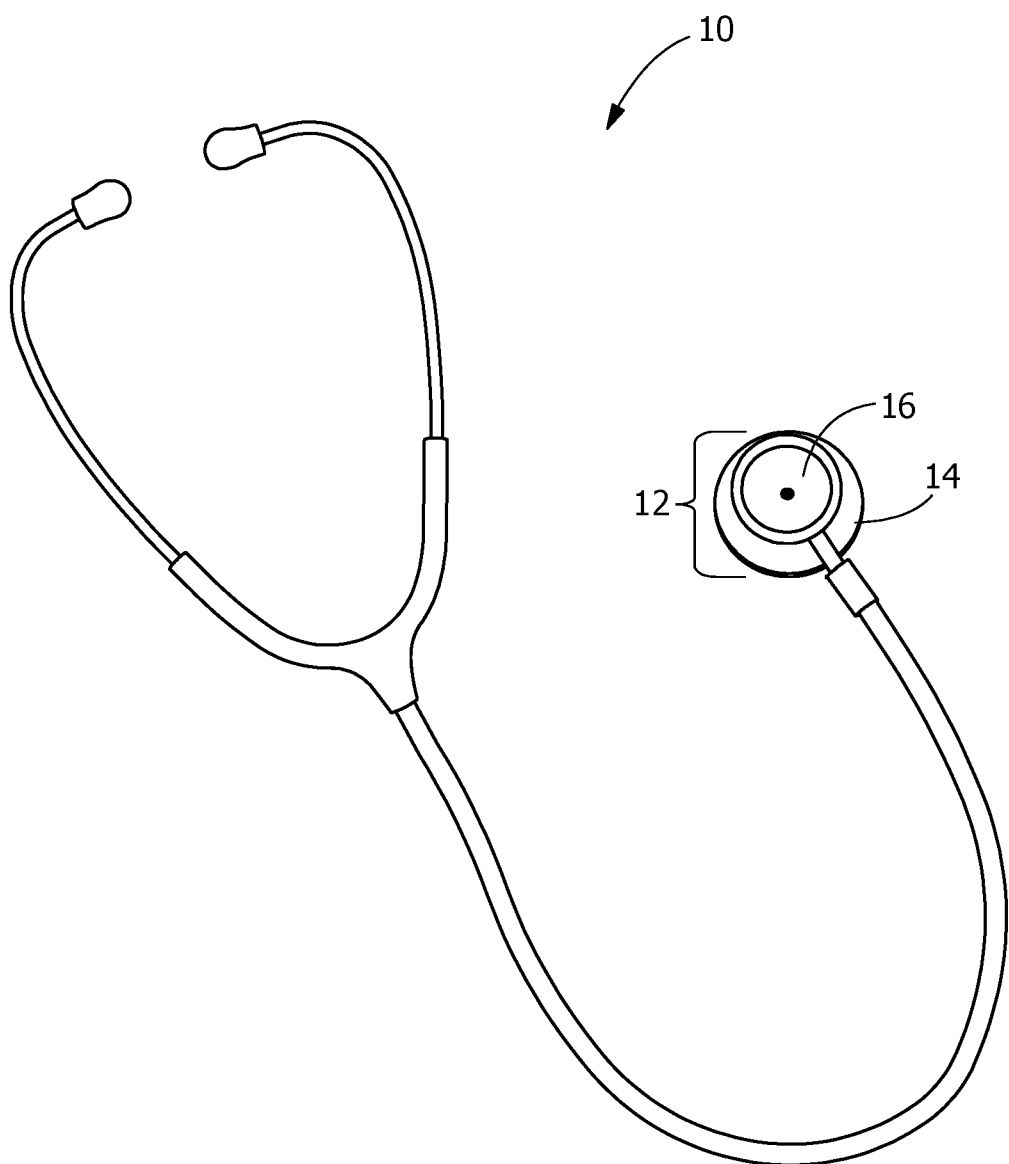
FIG. 1 is a plan view of a prior art stethoscope.

The present disclosure is directed to a sterile cover and dispenser for covering a stethoscope 10 such as shown in FIG. 1, which is of well-known construction. The cover and dispenser permit a user, such as a medical professional or medical practitioner or practitioner, to utilize stethoscope 10 without touching or physically contacting a stethoscope head 12 of stethoscope 10, which stethoscope head 12 typically including a diaphragm 14 and a bell 16. Furthermore, the cover is configured so as to permit removal of the cover without the user touching or physically contacting the portion of the cover that had previously touched or physically contacted the patient. Stated another way, the stethoscope head cover and stethoscope head cover dispenser of the present disclosure permit a practitioner to avoid touching or making physical contact with the stethoscope head or the patient, while also avoiding touching or making physical contact between the patient and the stethoscope head.

For purposes herein, the term "sterile" is intended to not only include a material and/or condition that is free from living germs or microorganisms, but also include less stringent materials and/or conditions. That is, the term "sterile" is intended to include any material and/or condition that would be suitable for use with a stethoscope or other medical device or device as described herein.

Figure 2:
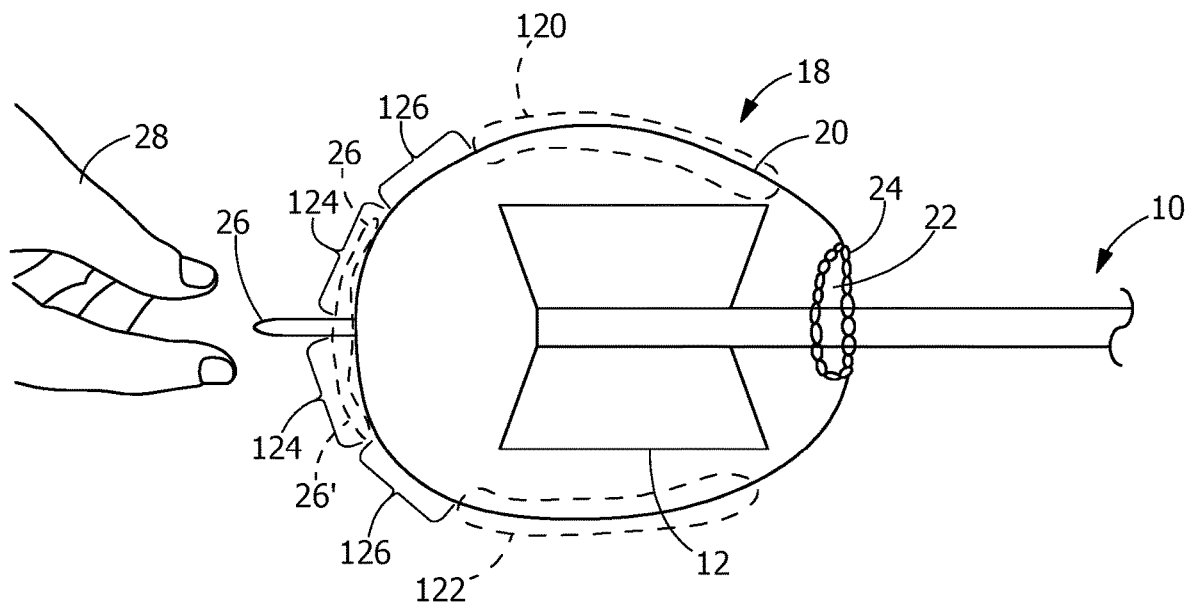
FIG. 2 is a cutaway view of a stethoscope head of FIG. 1 surrounded by an exemplary cover.

FIG. 2 shows a pouch or cover 18 including a hollow flexible body 20 having an open end or opening 22 and a closed end opposite opening 22, which cover 18 being adapted to receive or that is sufficiently large to surroundingly receive stethoscope head 12. In one embodiment, body 20 may be stretchable. In one embodiment, body 20 may be essentially non-stretchable. In one embodiment, body 20 may be essentially non-flexible. In one embodiment, all or one of more portions of body 20 may be flexible, non-flexible, stretchable, or non-stretchable. In one embodiment, opening 22 at least partially includes an elastic material 24, permitting opening 22 to be temporarily enlarged sufficiently for stethoscope head 12 to be inserted through opening 22 and then inside of body 20, after which insertion of stethoscope head 12, opening 22 being permitted to contract in size for enhancing retention of stethoscope head 12 in body 20 during the single use of the cover. In one embodiment, elastic material 24 is a band. In one embodiment, body 20 is composed of elastic material. As shown, body 20 includes at least one tab or flap or protrusion 26 positioned opposite opening 22 and extending outwardly from the surface of body 20. In one embodiment, protrusion 26 is folded or collapsed or flattened state or condition or position of cover 18, as will be discussed in greater detail below for storage in a dispenser, the protrusion is designated as protrusion 26' and rests against adjacent portions 124 of body 20, such as shown in FIGS. 2 and 3A. In one embodiment, the protrusion is sized lengthwise such that there is a spacing 126 or separation between patient contacting regions 120, 122 of cover 18 opposite corresponding portions of stethoscope head 12, and the furthest extent of protrusion 26', such as in the event that protrusion 26' remained positioned against adjacent portions 124 of body 20 when cover 18 is in its extended position or condition during use, and requiring a user 28 (FIG. 2), such as one or more fingers and a thumb of one hand of user 28, to dislodge or actuate the protrusion from its "flattened position" designated as protrusion 26' toward its extended position designated as protrusion 26, the fingers of user 28 would not physically contact or touch patient contacting regions 120, 122 of cover 18. In one embodiment, user 28 may orient stethoscope 12 such that protrusion 26' is positioned on the opposite side of or faces away from the patient contacting region 120, 122 that is to be brought into contact with the patient, preventing protrusion 26' from contacting the patient, and permitting user 28 to remove cover 18 by grasping protrusion 26' without touching or making physical contact with any of the stethoscope head, the patient, or the patient contacting region that had contacted the patient.

In one embodiment, protrusion 26 may be composed of a material that is the same as the cover material. In one embodiment, protrusion 26 may be composed of at least two layers of the cover material, providing protrusion 26 with greater rigidity compared to the rigidity of the cover. In one embodiment, protrusion 26 may be at least partially composed of a different material than the cover material. In one embodiment, protrusion 26 may be composed of a rigid or substantially rigid elongated member. In one embodiment, protrusion 26 may include a coating or have been partially immersed in a material providing enhanced stiffness or resulting in at least a portion of the protrusion having a tendency to extend outwardly from a surface of body 20, such as from adjacent portions 124 when cover 18 is in an extended or expanded or position or condition, permitting protrusion 26 to be grasped by a user, without the user contacting the stethoscope head 12, or the patient contacting regions 120, 122 of body 20. In one embodiment, such as shown in FIGS. 3A and 3B, an end of the protrusion is affixed to body 20, and upon insertion of stethoscope head 12 inside of body 20 (FIG. 3B), the stretching of material of body 20 being sufficient to actuate the protrusion from its flattened position, designated as 26' to its extended position 26. In one embodiment, upon insertion of stethoscope head 12 inside of body 20 (FIG. 3B), even in the absence of stretching of material of body 20, the protrusion may self-actuate from its flattened position, designated as 26' to its extended position 26, such as by a retention force, such as by material memory.

Figure 3:
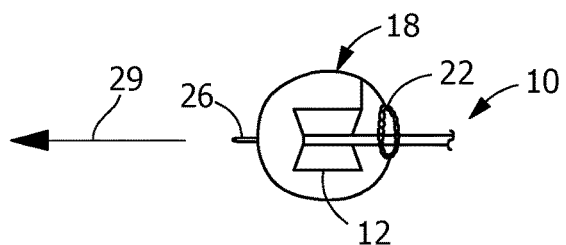
FIG. 3 is a cross-section of the stethoscope head and cover of FIG. 1 being subjected to a separation force.
Figure 3A:
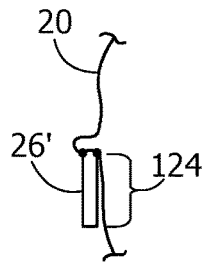
FIG. 3A is a partial view of the cover of FIG. 2 in a collapsed condition.
Figure 3B:
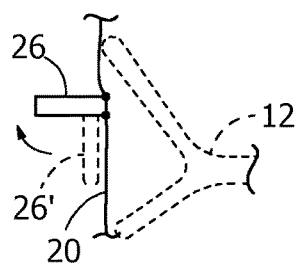
FIG. 3B is a partial view of the cover of FIG. 2 in an extended condition.

As further shown in FIG. 3, subsequent to placing the covered stethoscope head against a patient for monitoring the patient's medical condition, user 28 (FIG. 2) may grasp protrusion 26 and then apply a separation force 29 in a single direction to protrusion 26 and away from stethoscope head 12, permitting cover 18 to be removed from stethoscope head 12 without the user touching or physically contacting the portion of the cover that had previously touched or physically contacted the patient.

Figure 4:
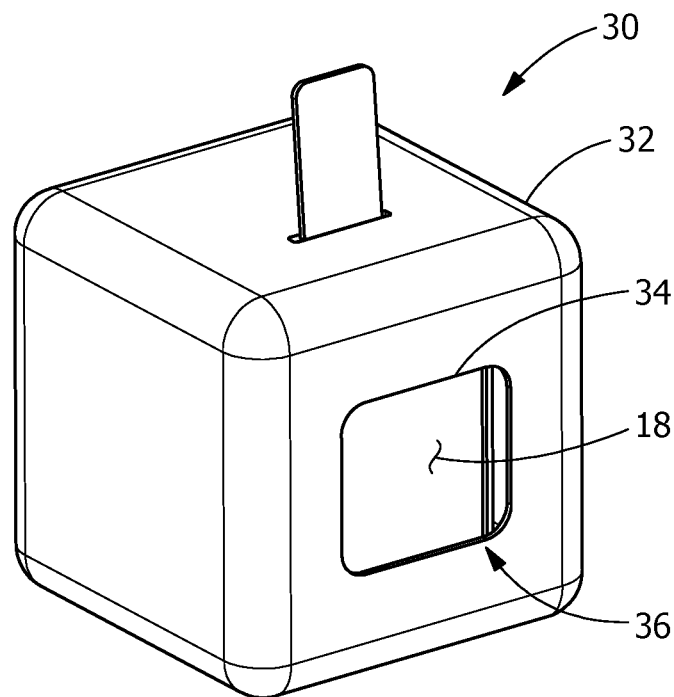
FIG. 4 is an oblique perspective view of an exemplary dispenser for covering a stethoscope head.
Figure 5:
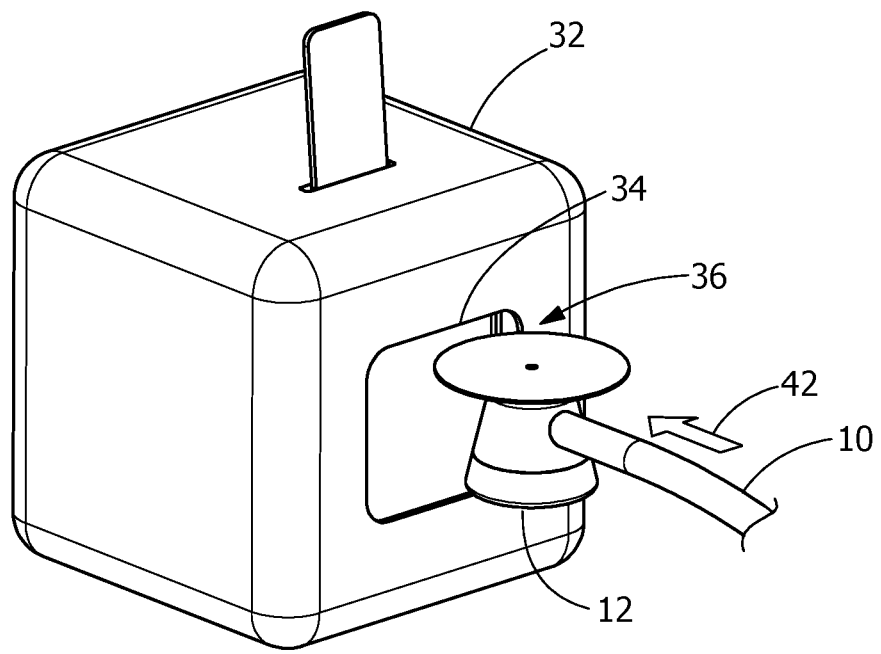
FIG. 5 is an oblique perspective view of the dispenser of FIG. 4 receiving a stethoscope head.

FIG. 4 shows an exemplary dispenser 30 for covering a stethoscope head 12 (FIG. 5). Dispenser 30 includes an enclosure 32 having an opening 34 for receiving stethoscope head 12 (FIG. 5) directed in an installation direction 42 (FIG. 5) in contact with cover 18 that is secured to a carrier 36.

Figure 6:
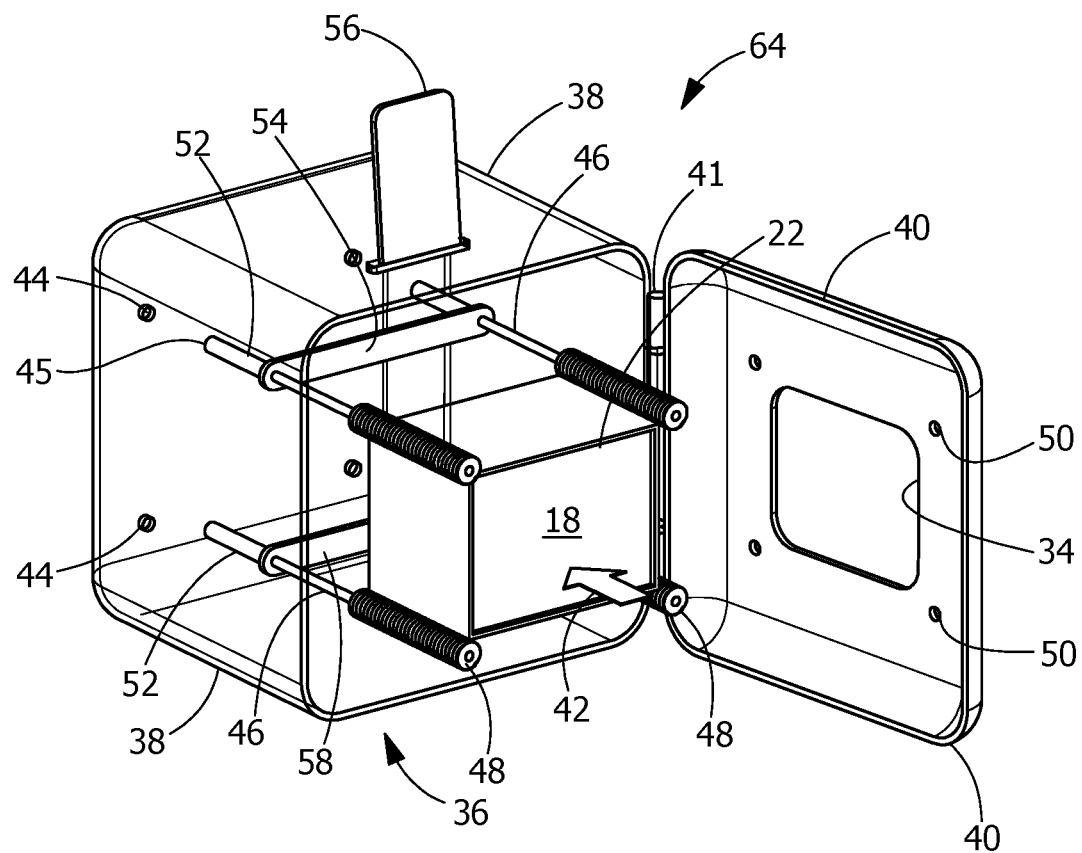
FIG. 6 is an oblique perspective view of an open, partially assembled dispenser of FIG. 4 with a transparent enclosure.
Figure 7:
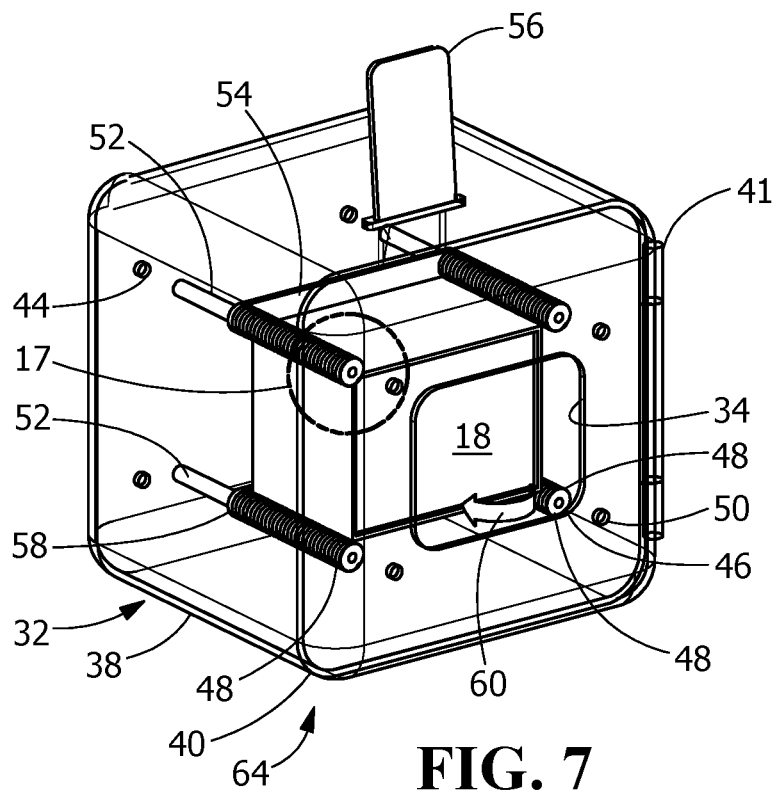
FIG. 7 is an oblique perspective view of the dispenser of FIG. 4 with a transparent enclosure.

FIGS. 6 and 7 show dispenser 30 in respective open and closed positions. Dispenser 30 includes enclosure portions 38, 40 pivotably connected by hinge 41 in a rotational movement 60 from the open position toward the closed position. Optionally, enclosure portion 38 includes mounting openings 44 for securing dispenser 30 to a vertical wall. Carrier 36 includes a plurality, such as four, guide/support rods 46 extending between enclosure portions 38, 40 when in a closed position. In one embodiment, when enclosure 32 is closed, one end of guide/support rods 46 extend from openings 45 formed in enclosure portion 38 to corresponding openings 50 formed in enclosure portion 40. A plurality of covers 18 include loops 48 through which corresponding guide/support rod 46 extend. When installed inside of enclosure 30, covers 18 are stretched between guide/support rods 46 and overlap opening 34. A resilient device 52, such as a helical spring is slid over, positioned at one end of each guide/support rod 46 adjacent enclosure portion 38 and compressed. A pair of positioners 54, 58 each have opposed openings for slidably engaging a corresponding pair of guide/support rods 46. In one embodiment, positioners 54, 58 are interconnected. Positioners 54, 58 are positioned between resilient devices 52 and the plurality of covers 18, applying a retention force of resilient devices 52 against loops 48 of covers 18 to collectively evenly urge covers 18 toward enclosure portion 40. As shown, positioner 54 includes a tab 56, permitting adjustment of positioner 54 if required, e.g., to advance covers 18 toward enclosure portion 40 to allow the cover 18 positioned immediately adjacent to enclosure portion 40 to be positioned in the "ready to receive" posture.

Figure 17:
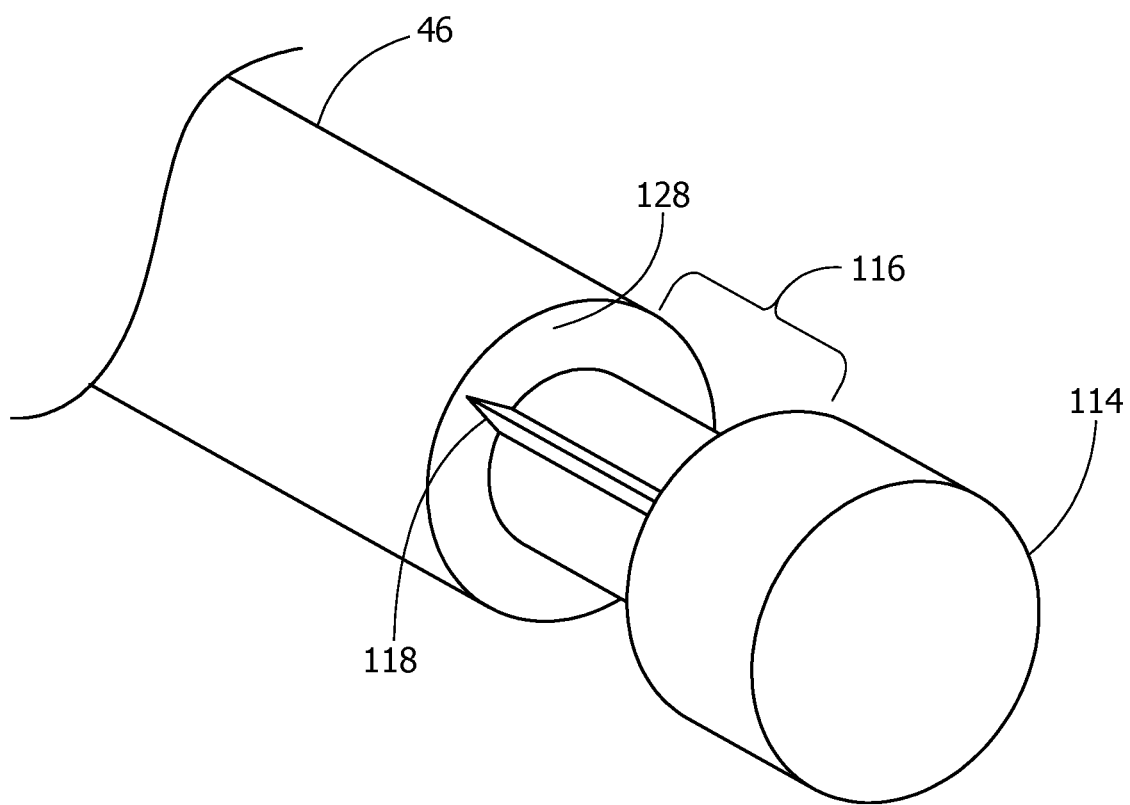
FIG. 17 is a partial, enlarged oblique perspective view of a portion of an exemplary carrier taken from region 17 of FIG. 7.

In response to stethoscope head 12 being directed in installation direction 42 (FIG. 6) through opening 34 of enclosure 32, stethoscope head 12 is brought into contact with the exposed cover 18 positioned most proximate to enclosure portion 40, attention is now brought to FIG. 17, which is an enlarged, partial view taken from region 17 of FIG. 7 of a corresponding end of guide/support rod 46. Adjacent each end 114 of guide/support rod 46 that is inserted into opening 50 of enclosure portion 40 (FIG. 7) is a recessed region 116 which is sized and positioned so as to receive a corresponding loop 48 (FIG. 7) of the cover 18 (FIG. 7). Each recessed region 116 includes a blade 118 oriented to outwardly face a corner of enclosure portion 40 (FIG. 7). In response to stethoscope head 12 being further inserted inside of enclosure 32 (FIG. 7) in contact with cover 18, the material of cover 18 conforms to surroundingly receive stethoscope head 12, and upon further insertion, the cover material is rendered taunt, the cover material inwardly drawing loops 48 (FIG. 7) against a portion of shoulder 128 and blade 118 of recessed region 116. In response to sufficient insertion of stethoscope head 12, loops 48 are severed by the corresponding blades 118, effecting separation of cover 18 from guide/support rods 46. The newly exposed cover 18, and the remaining covers 18, may be dispensed in a similar manner. This compact, construction defines an integrated cover/carrier package 64.

In one embodiment, if the guide/support rods 46 did not extend into enclosure portion opening 50 of enclosure portion 40, tab 56 of positioner 54 may be actuated to "push off" or disengage loops 48 of cover 18 after having covered a stethoscope head.

Figure 8:
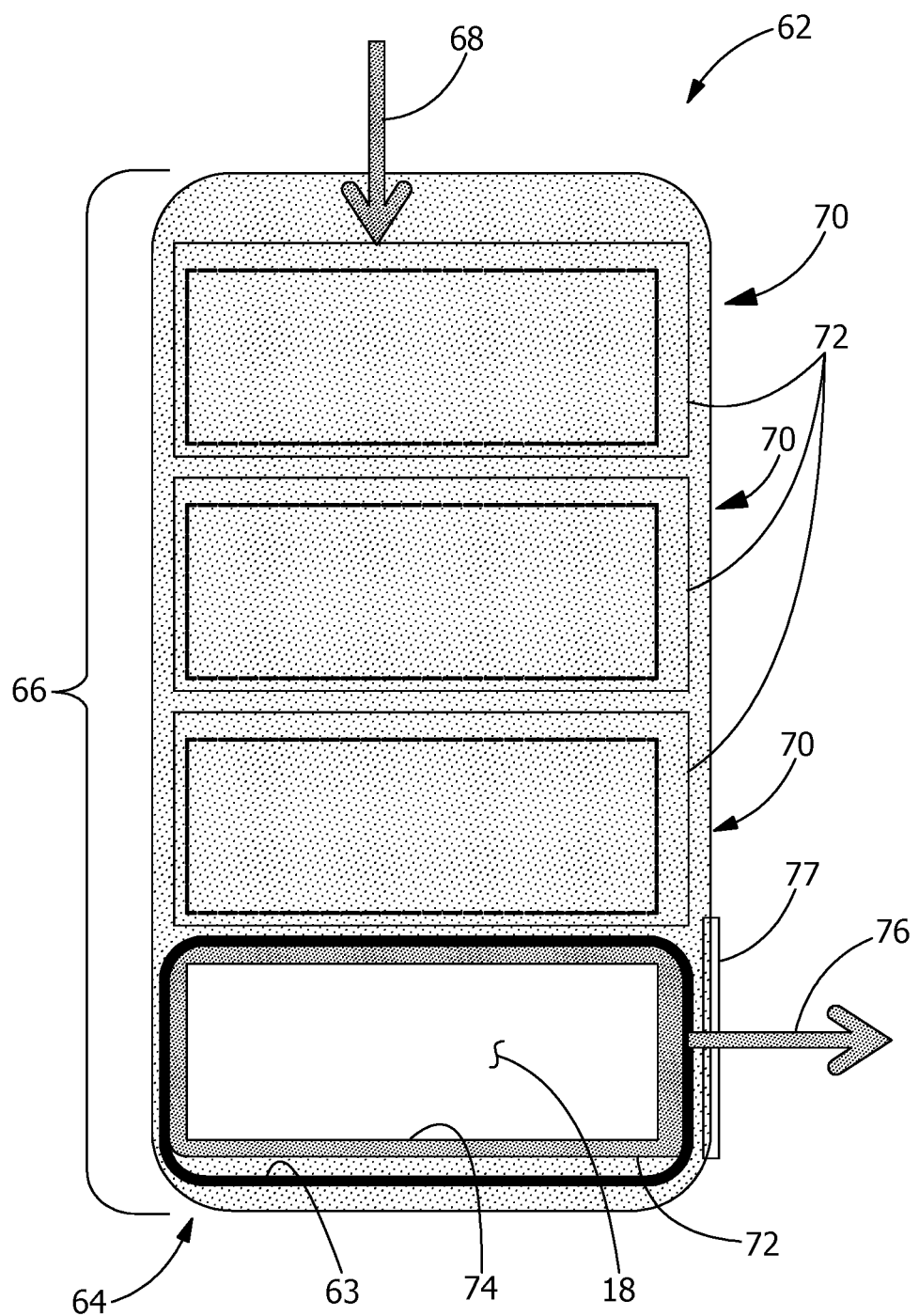
FIG. 8 is a front view of an exemplary dispenser for covering a stethoscope head.

As shown in FIG. 8, a dispenser 62 includes an enclosure 66 adapted to store a plurality of integrated cover/carrier packages 64 individually stored in a module 72, such as a fiberboard box. Each module 72 includes a perforated opening 74 (achieved by removal of material from module 72 (not shown) surrounded by perforations that define perforation opening 74) permitting access to covers 18. Enclosure 66 includes an opening 63 sized to permit access to perforated opening 74. That is, in a manner similar as shown in FIG. 5, stethoscope head 12 (FIG. 5) may be inserted through opening 63, then through opening 74 to contact cover 18. Once all covers have been expended or removed from module 72 aligned with opening 63, module 72 is removed in removal direction 76 via an access opening 77 that may be covered by a movable panel (not shown). Upon removal of the empty module 72 from enclosure 66, the next module 72 immediately vertically above the empty module 72 and defining an unopened cover/carrier package 70 is loaded in loading direction 68 as a result of gravity, wherein upon removal of material from module 72 defined by perforated opening 74, the newly exposed cover 18, and the remaining covers 18, may be dispensed in a similar manner.

Figure 9:
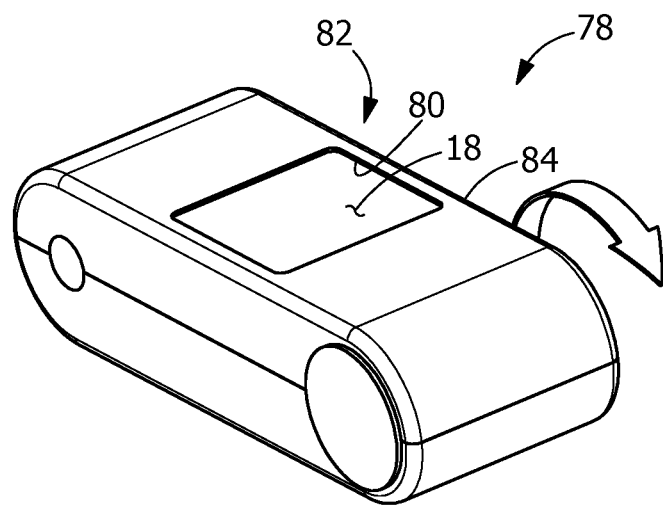
FIG. 9 is an oblique perspective view of an exemplary dispenser for holding several modules of dispensing stethoscope head covers.
Figure 10:
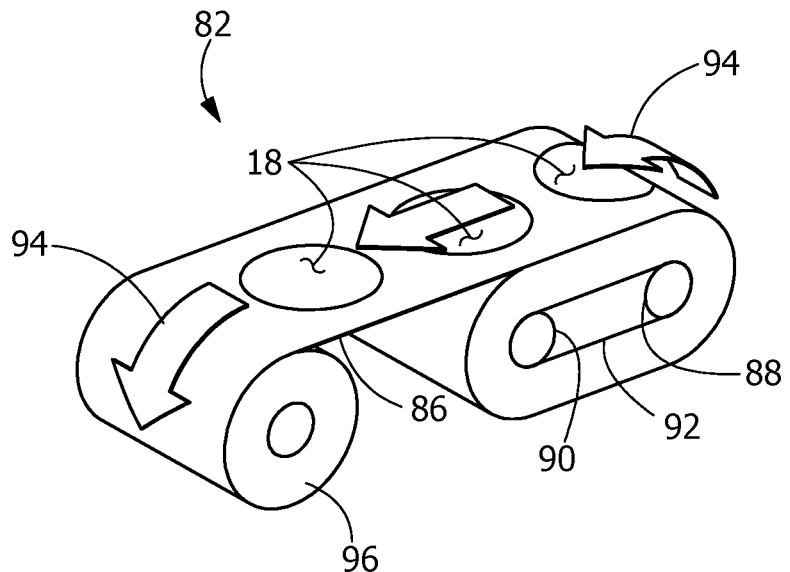
FIG. 10 is an oblique perspective view of an exemplary stethoscope cover carrier.
Figure 14:
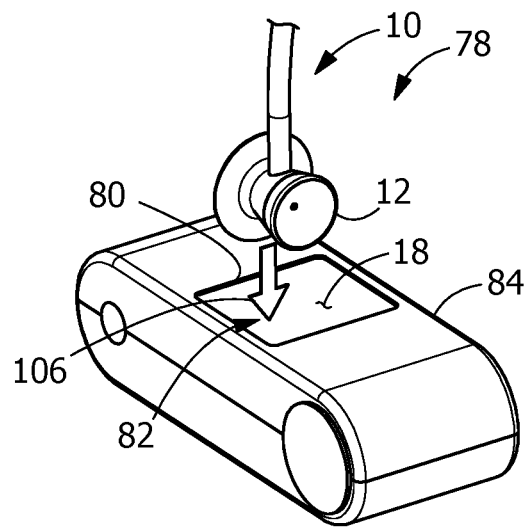

FIG. 9 shows an exemplary dispenser 78 having an opening 80 formed in an enclosure 84 for dispensing covers 18 from carrier 82. As shown in FIG. 10, one embodiment of carrier 82 includes a strip 86 adapted to secure a plurality of spaced apart compacted covers 18 thereon for selective access for covering stethoscope heads 12 (FIG. 14). As further shown in FIG. 10, feed rollers 88, 90 feed strip 86 in feed direction 94, permitting covers 18 to be sequentially accessed and removed from strip 86 via opening 80 (FIG. 9), the expended strip 86 being further fed in feed direction 94 to take-up reel 96. Optionally, an additional feed roller 90 is operatively connected via belt 92 to feed roller 88 in order to accommodate a carrier 86 of greater length in order to provide an increased number of covers 18.

Figure 11:
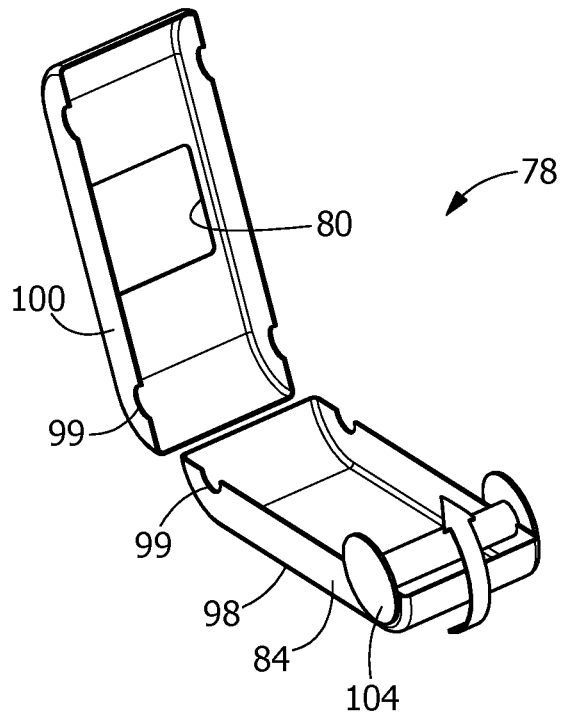
FIG. 11 is an oblique perspective view of an opened enclosure of the dispenser of FIG. 9.
Figure 12:
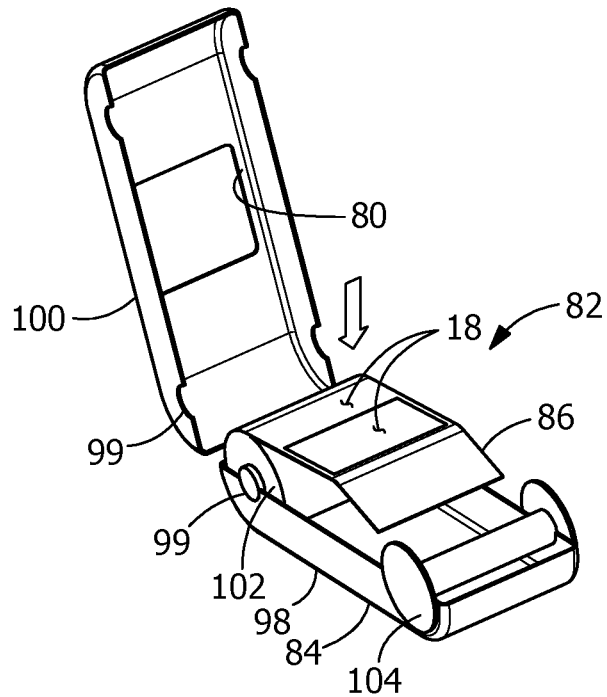
FIG. 12 is an oblique perspective view of the opened enclosure of the dispenser of FIG. 9 including an exemplary stethoscope cover carrier.
Figure 13:
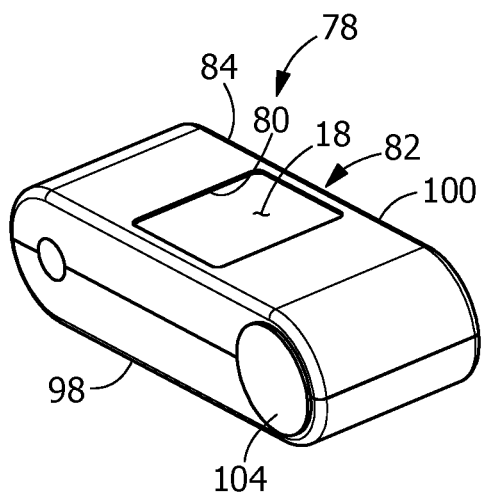
FIGS. 13-16 are sequential oblique perspective views showing the operation of an exemplary stethoscope cover dispenser.
Figure 15:
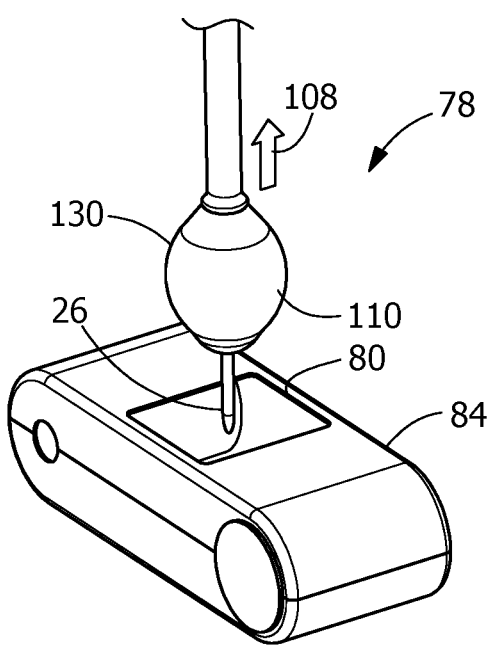
Figure 16:
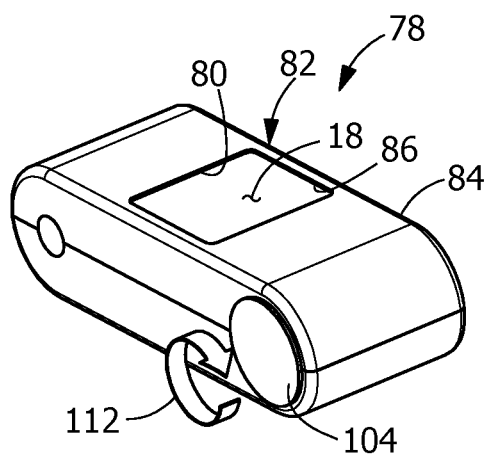

FIGS. 11-16 show a sequence of loading and operating dispenser 78. As shown in FIG. 11, enclosure 84 is opened by pivotably separating enclosure portions 98, 100, exposing recesses 99 formed in enclosure portions 98, 100 for receiving corresponding take-up roller 104 and feed roller 102 (FIG. 12). As shown in FIG. 12, feed roller 102 that includes carrier 82, which includes carrier strip 86 wrapped around feed roller 102, is positioned in corresponding recesses 99 of enclosure portion 98, followed by engaging take-up roller 104 and carrier strip 86, i.e., wrapping the loose end of carrier strip 86 around take-up roller 104. Once enclosure portions 98, 100 are brought together to form the intact or assembled enclosure 84, as shown in FIG. 13, FIG. 14 shows stethoscope head 12 directed in installation direction 106 through opening 80 of enclosure 84 in contact with a corresponding cover 18 exposed or aligned with opening 80 of enclosure 84. Stethoscope head 12 is further directed inside of enclosure 84 until cover 18, which surrounds stethoscope head 12, designated as covered head 110 (FIG. 15) is separated from carrier strip 86. Optionally, dispenser 78 may include an electronic triggering mechanism to separate the cover from the cover strip, such as in response to the stethoscope head being inserted through the opening a sufficient insertion depth. Once cover 18 is separated from carrier strip 86, as shown in FIG. 15, covered stethoscope head 110 is removed from enclosure 84 through opening 80 in a removal direction 108. As further shown in FIG. 15, protrusion 26 extends outwardly from the surface of the extended or expanded cover 130 of covered stethoscope head 110, permitting subsequent removal of the cover after use without the user 28 (FIG. 2) contacting the portion of the cover that contacts with the patient (not shown), in a manner previously discussed. Finally, as shown in FIG. 16 take-up roller 104 is urged into a rotational movement 112 to advance carrier strip 86 of carrier 82 until the next cover 18 is aligned with opening 80 to be dispensed in a manner previously discussed.

In one embodiment, instead of separate take-up and supply rollers, the carrier may include a cartridge integrating the rollers and carrier strip, similar to those usable in cameras or typewriters.

It is appreciated by those having ordinary skill in the art that the cover of the present invention may be utilized for covering articles other than stethoscopes, such as ultrasound probes, transducers and other medical devices that otherwise come into direct contact with the patient. In addition, the cover is not limited to devices for use in the medical field. The present invention contemplates being used for covering any device that may be inserted in a cover using one or more tabs positioned on the cover as previously discussed.

It is to be understood that the dispensers of the present invention may be manually advanced, or may be automated to automatically advance the carrier, such as in response to withdrawal of the covered stethoscope head.

Figure 18:
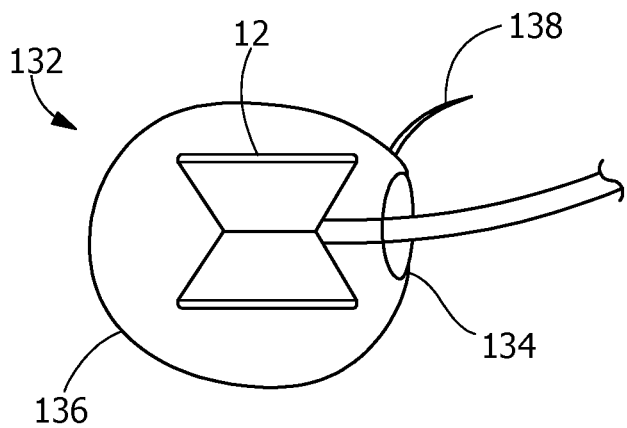
FIG. 18 is a side view of an exemplary cover surrounding a stethoscope head.
Figure 19:
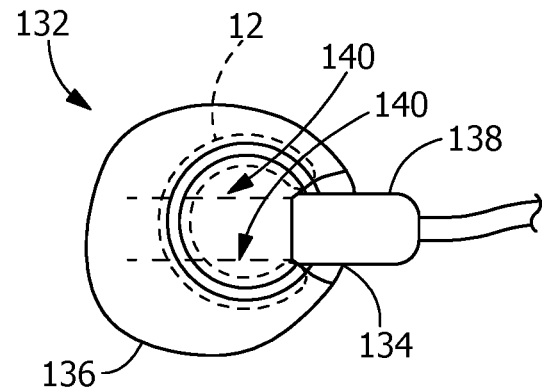
FIG. 19 is a plan view of the cover surrounding the stethoscope head of FIG. 18.
Figure 20:
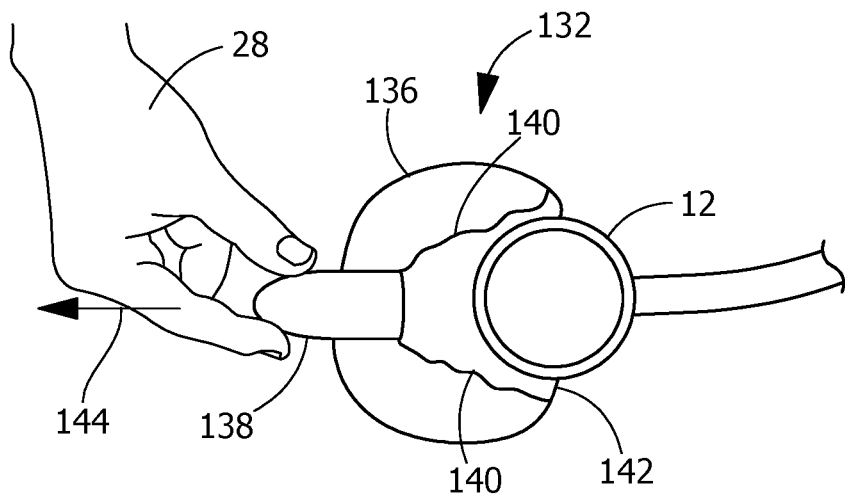
FIG. 20 is a plan view of the cover with a distorted opening for permitting removal of the stethoscope head from the cover.

FIGS. 18-19 show respective side and plan views of an exemplary pouch or cover 132 surrounding stethoscope head 12. Cover 132 includes a hollow flexible or non-flexible body 136 having an opening 134 that is sufficiently large to surroundingly receive stethoscope head 12. A tab or protrusion 138 is positioned at or near open end or opening 134. As shown, protrusion 138 is positioned between and proximate to a pair of weakened regions 140 such as perforations or areas of reduced thickness of body 136 extending along cover 132 to opening 134. In one embodiment, the pair of weakened regions 140 are generally parallel to each other. In one embodiment, at least a portion of the pair of weakened regions 140 may be non-parallel to each other. In one embodiment, protrusion 138 is positioned to one side of weakened regions 140. In one embodiment, protrusion 138 is positioned near a single weakened region 140. As shown in FIG. 20, in response to user 28 grasping protrusion 138 and applying a force 144 in a direction away from stethoscope head 12, at least one of weakened regions 140 rupture, forming an enlarged distorted opening 134 for permitting stethoscope head 12 to be removed from cover 132 without user 28 contacting stethoscope head 12 in a manner as previously discussed.

FIG. 21 shows a receptacle 146 adapted to receive a container 148 (FIG. 22) for collectively defining a dispenser 150 (FIG. 22) for dispensing pouches or covers for covering a stethoscope, as will be further discussed. In one embodiment, receptacle 146 is adapted to be secured to a vertical support surface, such as a wall of a building structure (not shown) for conveniently positioning dispenser 150 (FIG. 22) proximate a user wearing or holding a stethoscope in preparation of treatment of a patient, helping to visually prompt the user to install the stethoscope cover over the stethoscope head prior to treating the patient. In one embodiment, receptacle 146 may be adapted to be placed on, or placed on and secured to a non-vertical support surface, such as table top. As further shown in FIG. 21, receptacle 146 includes a body 152 having a plurality of interconnected walls or wall portions 154, 156, 158 defining an internal volume 176 for securing container 148 (FIG. 22) therein. For example, one end of wall 154 is connected to wall 156 that is connected to wall portion 160 which is opposite wall 154. The opposite end of wall 154 is connected to wall 158 that is connected to wall portion 162 that is opposite wall 154. Wall 156 is opposite to and generally parallel to wall 158, and wall 154 is opposite to and generally parallel to wall portions 160, 162. As shown, wall portions 160, 162 are separated by a space 164 and collectively support the same corresponding surface of container 148 (FIG. 22).

It is to be understood that while the walls of receptacle 146 are disclosed as corresponding to surfaces of a rectangular container, the walls of receptacle 146 are not so limited, and may be adapted to receive any container having a cylindrical profile defining any shape. As further shown in FIGS. 21 and 22, walls 156, 158 include at least one opening 166 sufficiently sized to permit an observer to discern the presence of container 148 (FIG. 22) having only a vantage point of one of walls 156, 158. In one embodiment, walls 156, 158 include a plurality of openings 166 forming an aesthetically pleasing pattern. As further shown, a tab 168 is connected to wall 154 proximate an end 170 of body 152 for vertically supporting container 148 that has been received in internal volume 176 of receptacle 146 through an opening 172 at an end 174 opposite end 170 of body 152, once body 152 has been secured to a vertical support surface, such as a wall of a building structure.

As further shown in FIG. 22, wall portions 160, 162 of dispenser receptacle 146 include several beneficial features for interacting with a container 148 inserted into and supported inside of receptacle 146. For example, cooperating slots 178, 180 of respective wall portions 160, 162 in combination with space 164 separating the wall portions 160, 162 define a continuous, unobscured opening 182 permitting viewing of indicia 184 that identifies the contents or product information of container 148, such as "Stethoscope Cover". Additionally, slots 186, 188, 190 formed in wall portion 160 in combination with space 164 separating wall portions 160, 162 define respective viewing regions 192, 194, 196, permitting viewing of respective indicia 198, 200, 202 that provides helpful usage instructions includes product description information and product installation steps on container 148, such as "1. Pull", "2. Insert", "3. Release", relating to a tab 204 of the "next available" cover or pouch 206 as will be further discussed.

Figure 31:
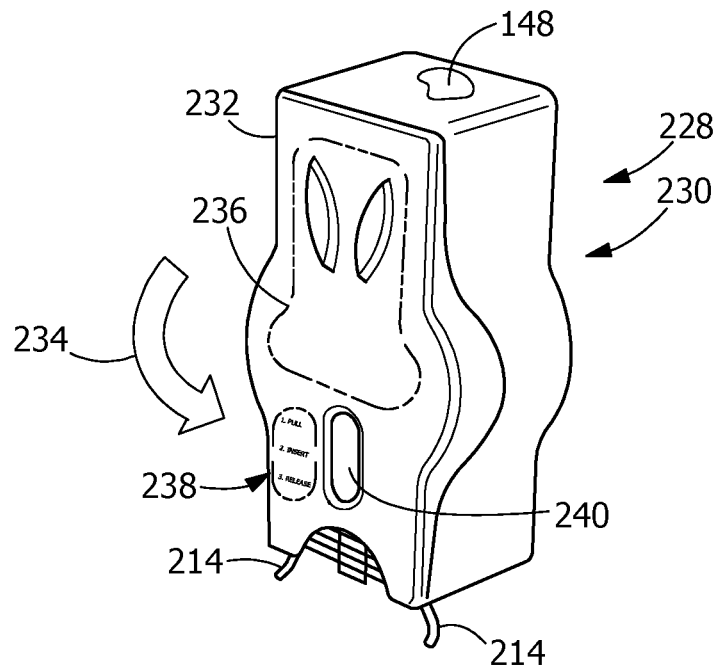
FIG. 31 is an oblique perspective view of an exemplary dispenser for dispensing covers for covering a stethoscope head.
Figure 31A:
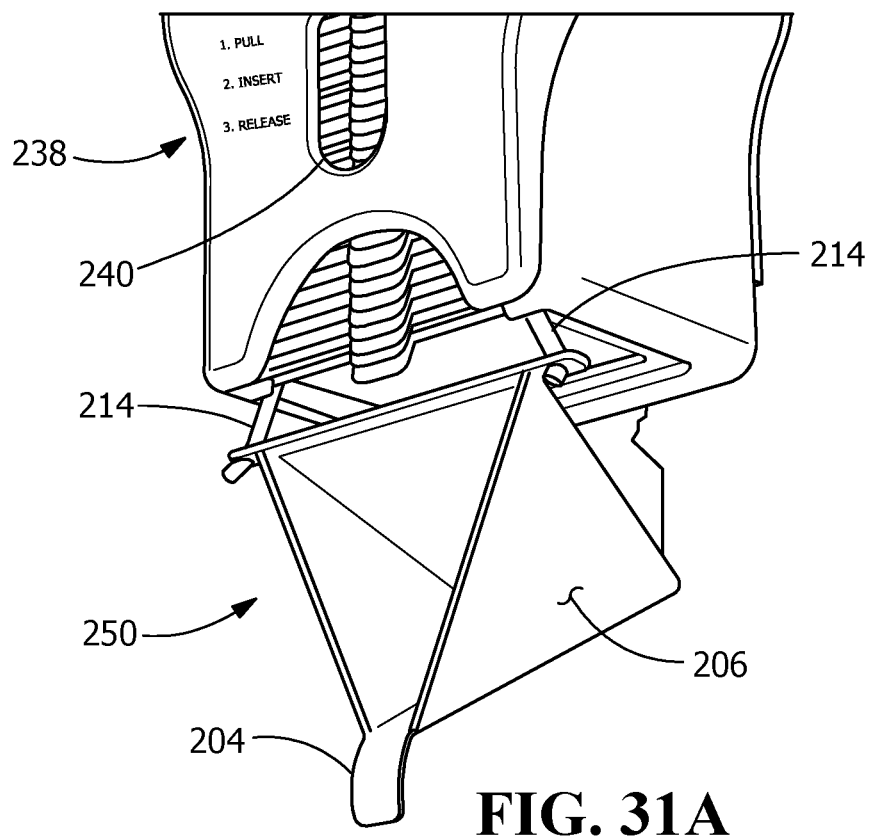
FIG. 31A is a partial, enlarged view of the dispenser of FIG. 31.
Figure 32:
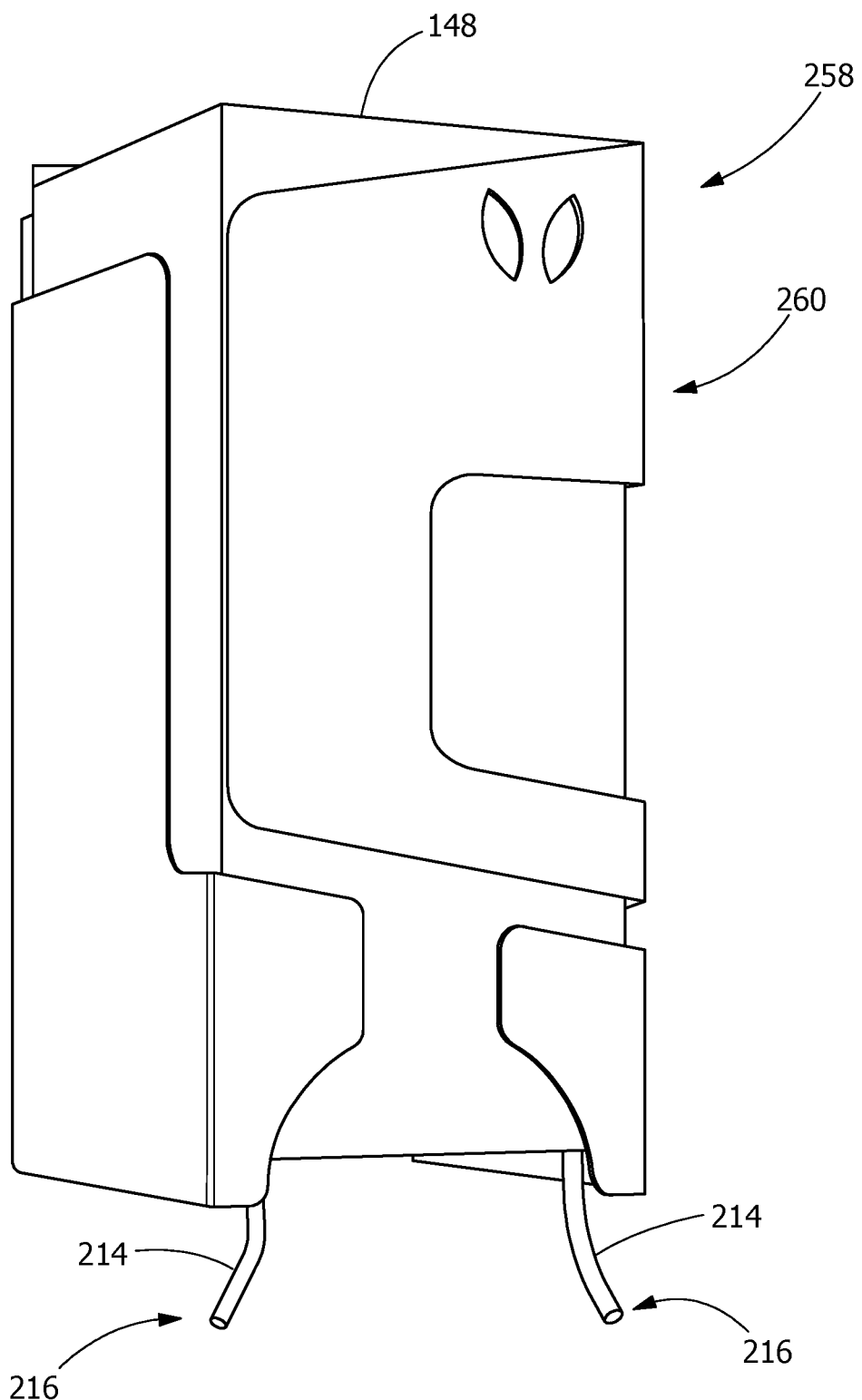
FIG. 32 is an oblique perspective view of an exemplary dispenser for dispensing covers for covering a stethoscope head.

FIGS. 31 and 31A show an exemplary dispenser 228 including a receptacle 230 having a wall 232 rotatable in a movement direction 234 relative to the remaining portion of dispenser 228 for receiving container 148 containing pouches for covering stethoscope heads as previously discussed. As shown, wall 232 includes indicia 236 relating to brand name or identification of product dispensed, indicia 238 relating to instructions for using the dispenser, and a viewing window 240 showing the amount of remaining pouches in the dispenser. Any suitable dispenser arrangements may be used, such as exemplary dispenser 258 including a receptacle 260 as shown in FIG. 32.

Figure 24:
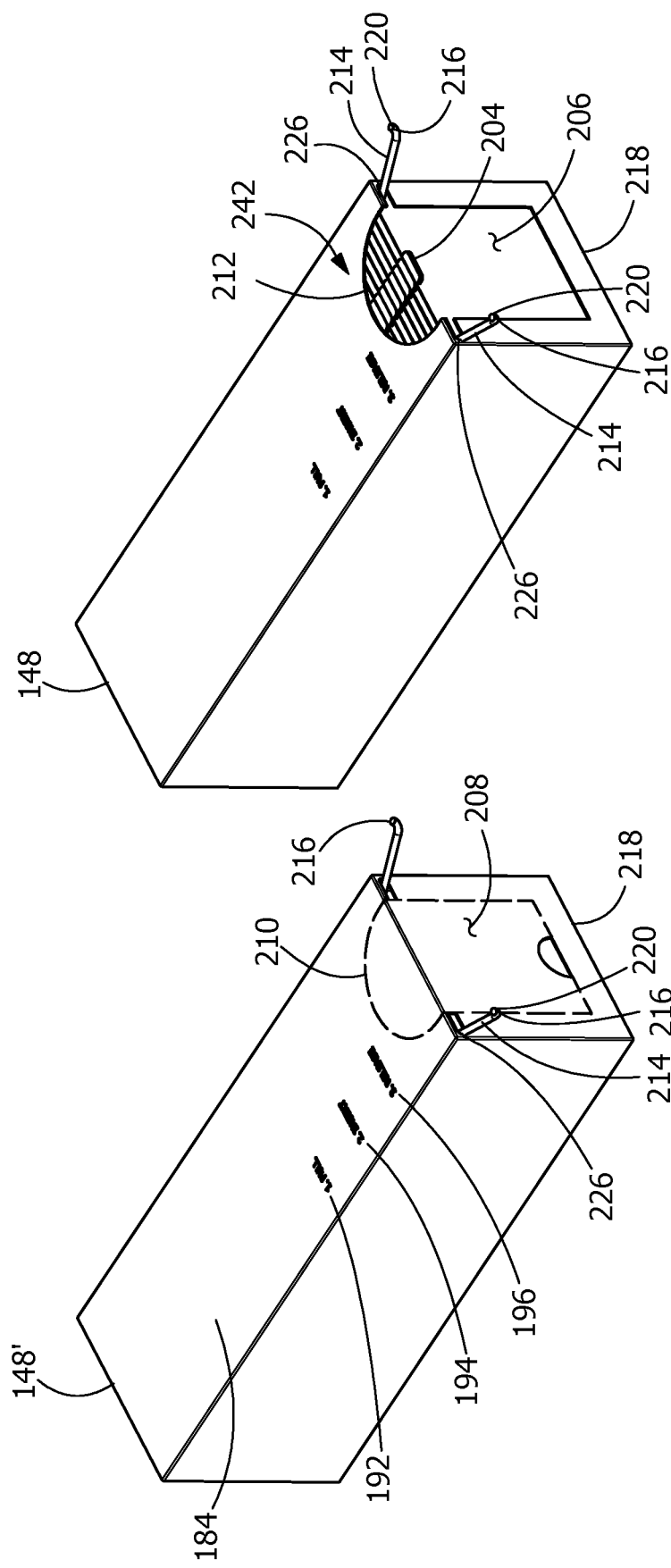
FIG. 24 is an oblique perspective view of an unopened container of FIG. 22 adjacent an opened container.

As shown collectively in FIGS. 22, 23, and most notably in FIG. 24 (showing an unopened container 148' (a removable cover or lid 208 secured by perforations 210 (intact)) or other mechanisms positioned proximate to an opened container 148 (lid 208 removed along perforation 210, exposing opening 212)) container 148 is now discussed. For purposes herein, unless stated otherwise, the term "container" is intended to refer to an opened container. As further shown in FIG. 24, container 148 contains a pair of elongated members 214, each member 214 terminates at a tip 216 proximate an end 218 of container 148 corresponding to end 170 (FIG. 22) of body 152 (FIG. 22) of dispenser receptacle 146 (FIG. 22) when container 148 is installed in the receptacle. Each tip 216 includes a retainer 220 such as an enlarged end, recess, notch, a directional change portion, such as a hook, relative to a proximal portion of the elongated member or other suitable feature for engaging a corresponding retainer 222 (FIG. 25) of support structure 224 (FIG. 25) of pouch 206 (FIG. 25) as will be further discussed. In one embodiment, the pair of elongated members are connected to one another.

As shown in the embodiments, such as FIG. 24, tips 216 of elongated members 214 extend exterior of container 148 and 148' through corresponding openings 226 formed in container 148 and 148'. However, the present invention is not so limited as "tips proximate one end of container" contemplate many different arrangements. For example, in one embodiment, tips 216 may be fully contained within or inside or interior of container 148 and 148'. In one embodiment, tip 216 or a portion of elongated member 214 proximate to tip 216 may be bent or retracted (e.g., similar to a telescoping radio antenna) so that tip 216 is contained within or inside or interior of container 148 and 148', but upon removal of lid 208 from container 148' (becoming container 148) tips 216 may then be unbent or extended (e.g., similar to a telescoping radio antenna) to at least partially extend exterior of container 148. In one embodiment, tip 216 may be removable from a corresponding elongated member 214 of container 148 and 148', but upon removal of lid 208 from container 148' (becoming container 148) tips 216 may then be secured to its corresponding elongated member 214, such as tip 216 having an opening at one end that is received by its corresponding elongated member 214, or vice versa, tips 216 being "loose" within container 148', secured to the cover nearest lid 208 (interior or exterior of the container), secured to lid 208 (interior or exterior of the container), or other suitable arrangement. As further shown in FIG. 24, a plurality of collapsed pouches 242 are supported on elongated members 214 in preparation of being selectively and individually dispensed from container 148 as will be further discussed below.

Figure 25:
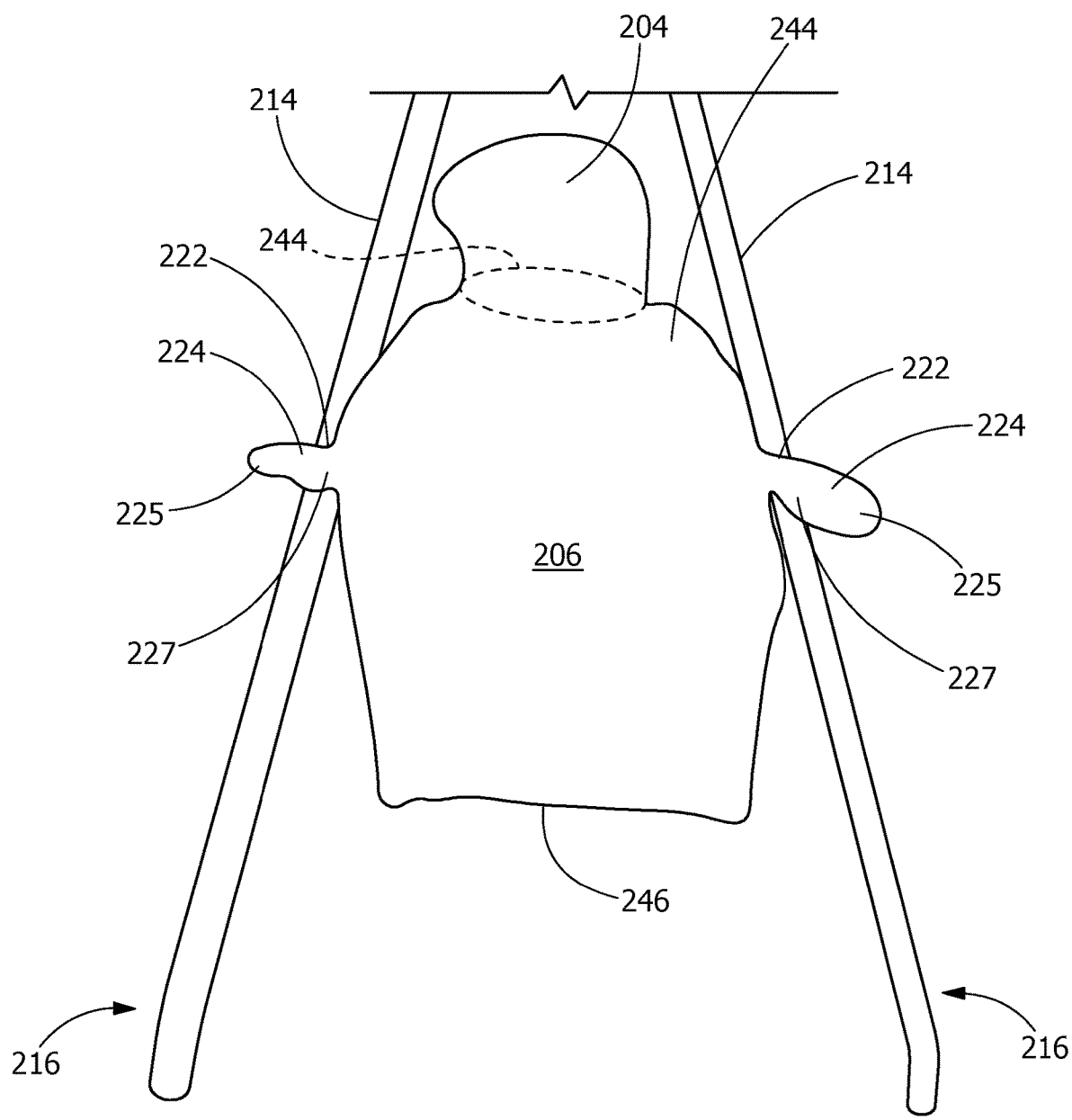
FIGS. 25-30 and 30A are cutaway views of the container of FIG. 22 showing sequential steps for covering a stethoscope head with an exemplary cover.

FIGS. 25-30 are cutaway views of the container 148 of FIG. 24 (i.e., the contents of the container with the outer walls of the container removed for purposes of clarity) showing sequential steps for covering a stethoscope head 12 (FIG. 28) with pouch 206. More specifically, FIGS. 25-30 are directed to showing how each pouch 206 of plurality of collapsed pouches 242 (FIG. 24) is manipulated for covering the stethoscope head. For purposes of simplicity and clarity, only one pouch 206 is shown in FIGS. 25-30. FIG. 25 shows an exemplary collapsed pouch 206 including an open end 244, a closed end 246, and a support structure 224 positioned proximate open end 244. In one embodiment, support structure 224 is a structural member that is secured to pouch 206 and extends outwardly from pouch 206. In one embodiment, support structure 224 is formed of pouch material (i.e., support structure 224 forms part of pouch 206) such as reinforced pouch material (e.g., overlapping portions of pouch material) and extends outwardly from pouch 206. Support structure 224 has a pair of retainers 222, each retainer 222 adapted to receive a corresponding elongated member 214 for supporting pouch 206 thereon. As further shown in FIG. 25, pouch 206 includes a removal tab or tab 204 positioned proximate open end 244. In one embodiment, the support structure is comprised of a pair of separate support structure portions 225, each support structure portion 225 having a retainer 227 adapted to receive a corresponding elongated member 214 for supporting pouch 206 thereon. In one embodiment, as shown in FIG. 25, elongated members 214 are arranged non-parallel to one another.

Figure 26:
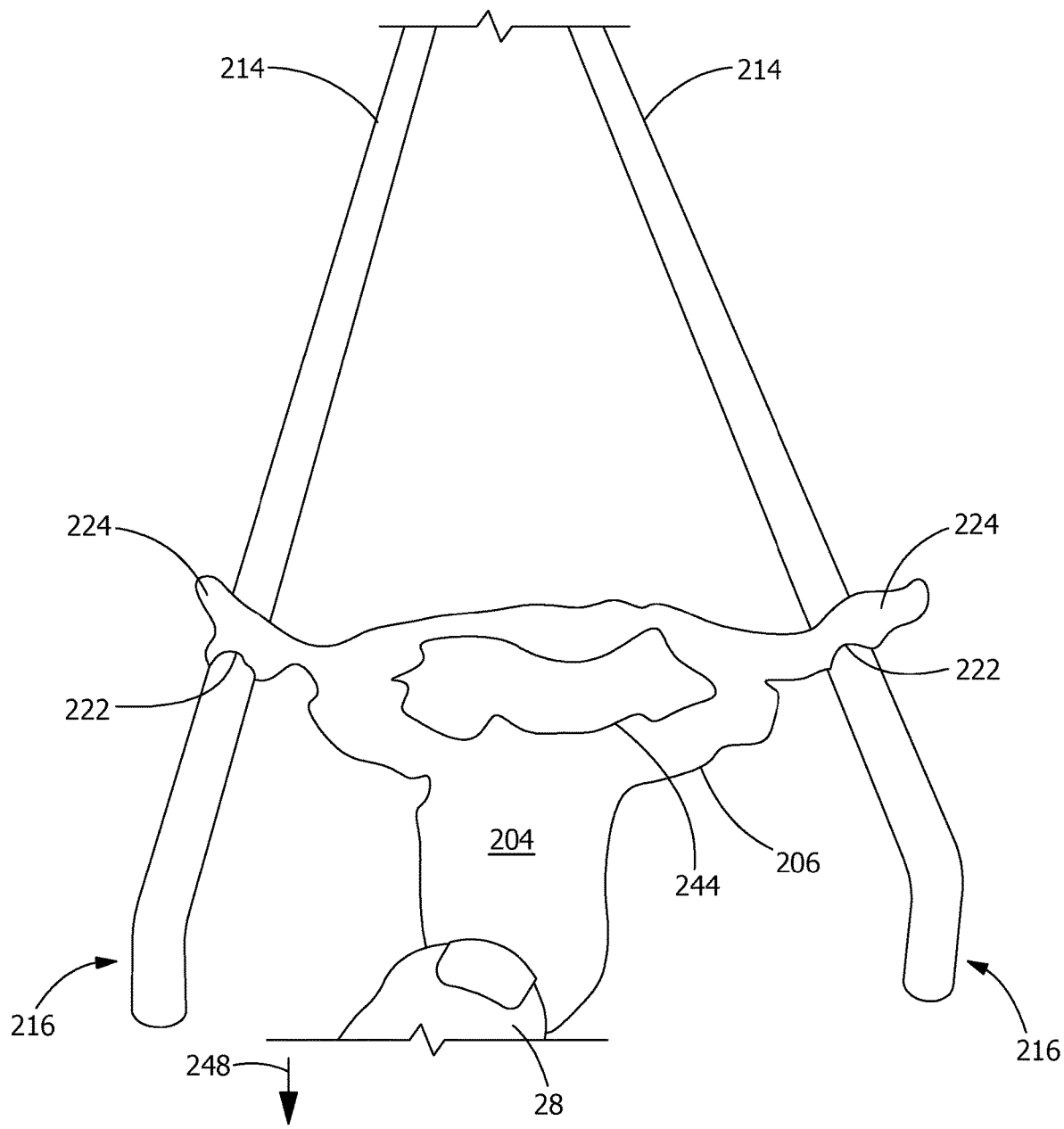
Figure 27:
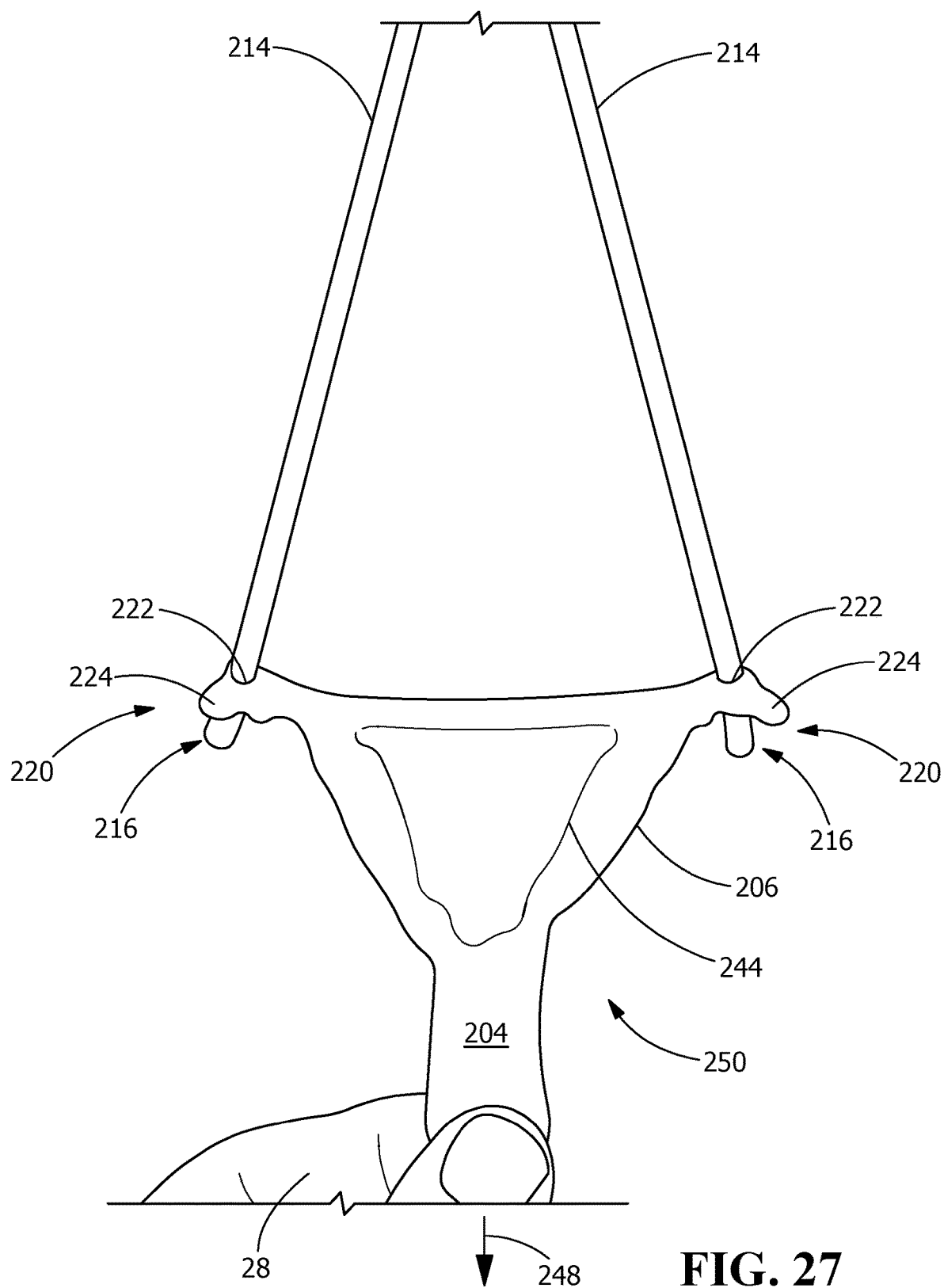

As shown in FIG. 26, a user 28 grasps tab 204 of the corresponding pouch 206 positioned nearest tips 216 of elongated members 214, and pulls tab 204 in a direction 248 toward tips 216 until tab 204 is proximate tips 216. In one embodiment, such as shown in FIG. 27 (which is representative to accessing the first pouch of a container full of pouches (see FIG. 22)), tab 204 of the corresponding pouch 206 positioned nearest tips 216 of elongated members 214 is already proximate tips 216. In response to a user 28 grasping tab 204 of the corresponding pouch 206 positioned nearest tips 216 of elongated members 214, and sufficiently pulling tab 204 in a direction 248 away from tips 216 such as a downward direction, retainers 220 of tips 216 of elongated members 214 engage corresponding retainers 222 of support structure 224 and no longer move relative to one another. As a result, further pulling tab 204 in a downward direction or downwards or in direction 248 away from tips 216 such as a downward direction or downwards, results in open end 244 of pouch 206 being urged toward an open position. In response to sufficiently further pulling tab 204 in direction 248 away from tips 216, open end 244 of pouch 206 defines an open position 250 defined by retainers 222 of support structure 224 and tab 204 for receiving a stethoscope head inside of pouch 206 while retainers 222 remain engaged with corresponding retainers 220 of tips 216 of elongated members 214.

It is to be understood that exemplary FIGS. 25-26 would not represent a realistic starting position for the corresponding pouch 206 positioned nearest tips 216 of elongated members 214, because as the pouches are being dispensed, the collapsed pouches are collectively urged on elongated members 214 toward tips 216, such as by one or more of gravity, a force generator, such as a spring or other suitable arrangement, or a low-grade adhesive interconnecting adjacent pouches. As a result, the starting position of tab 204 of the corresponding pouch 206 positioned nearest tips 216 of elongated members 214 (i.e., "the next available pouch") approximates tips 216 or is proximate tips 216, such as shown in FIG. 27.

Figure 28:
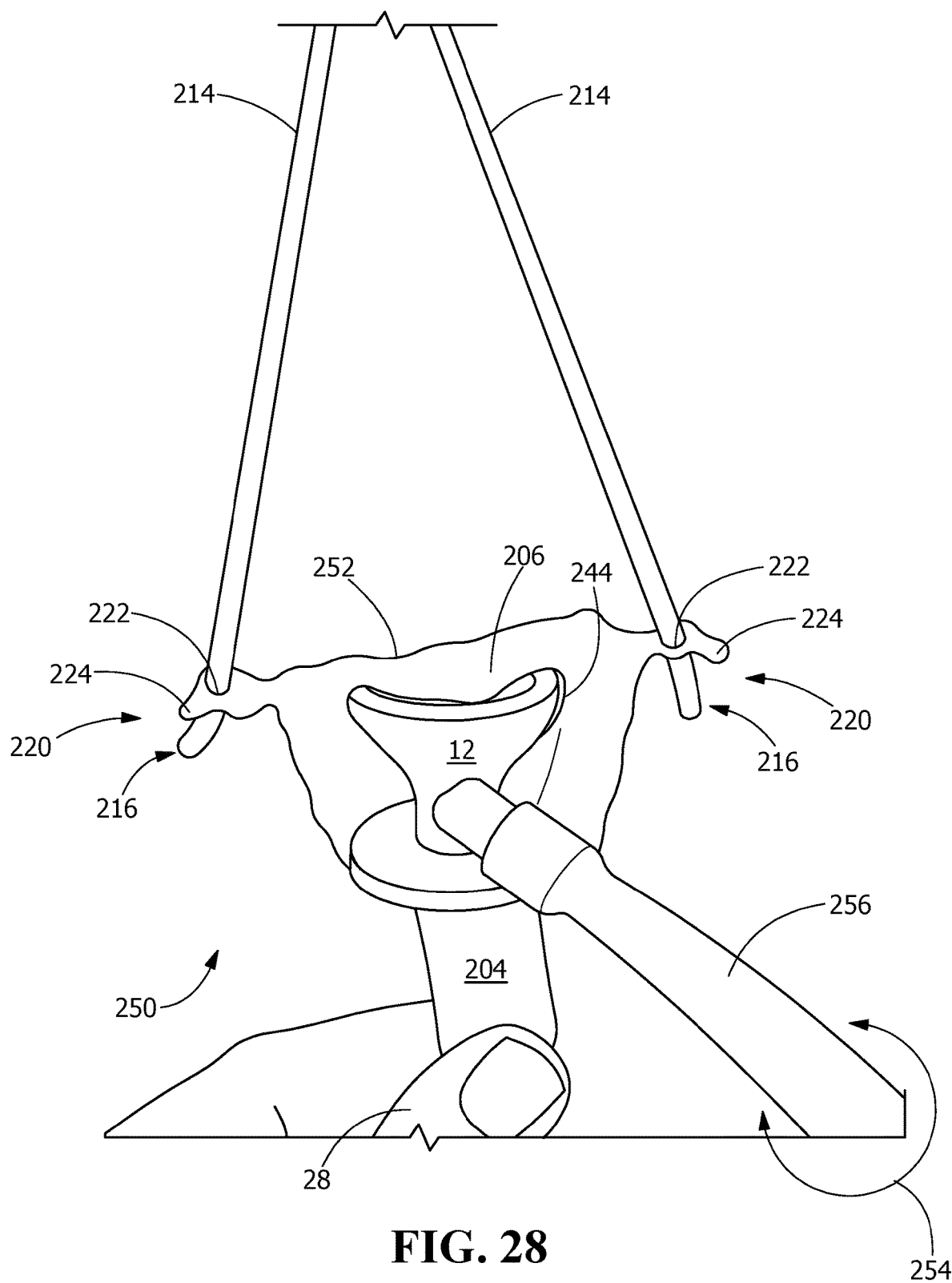
Figure 29:
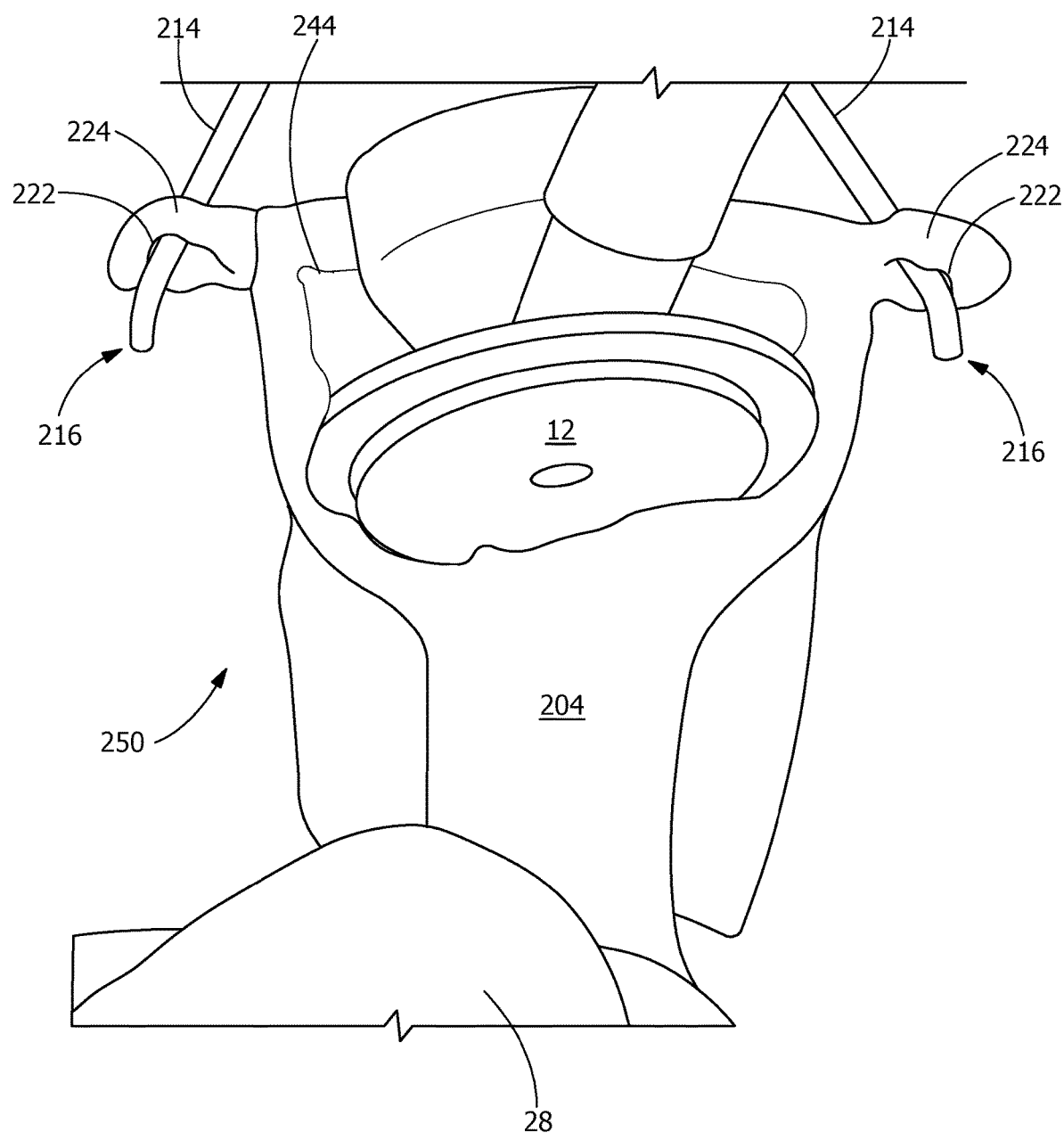

As shown in FIGS. 28-29, once open end 244 of pouch 206 defines open position 250, user 28 directs stethoscope head 12 inside of pouch 206. In one embodiment, simultaneously with the user directing stethoscope head 12 inside of pouch 206, user 28 orients the stethoscope head relative to tab 204. For example, some stethoscopes have opposed "listening portions" such as a diaphragm that is adapted to better monitor lung function and a bell that is adapted to better monitor vascular function. That is, depending upon the patient function that is to be monitored, the user could orient the stethoscope head such that the desired listening portion faces away from tab 204 or side 252, by rotating tubing 256 of the stethoscope in a rotational direction 254 relative to the pouch or even within the pouch itself.

Figure 30:
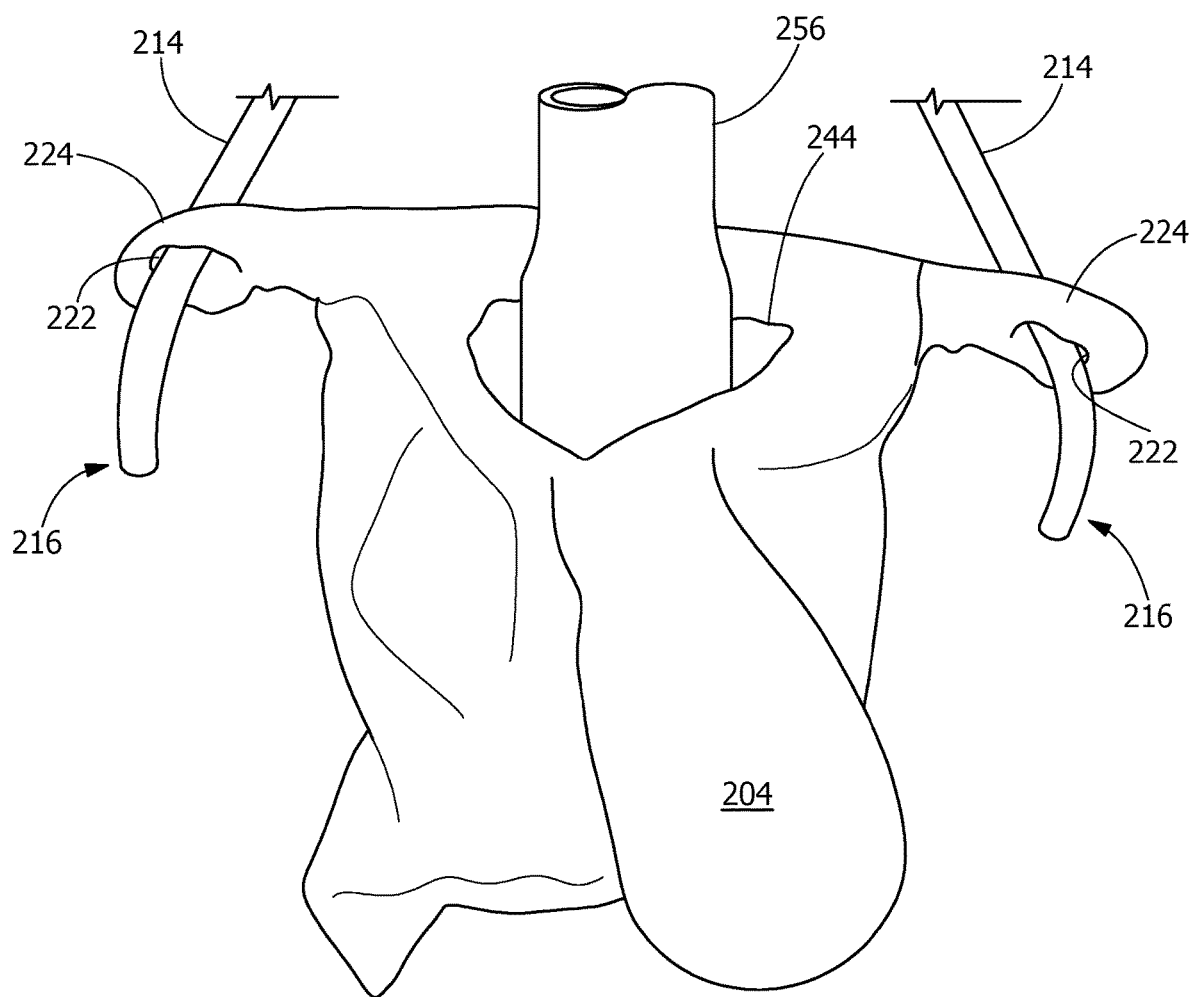
Figure 30A:
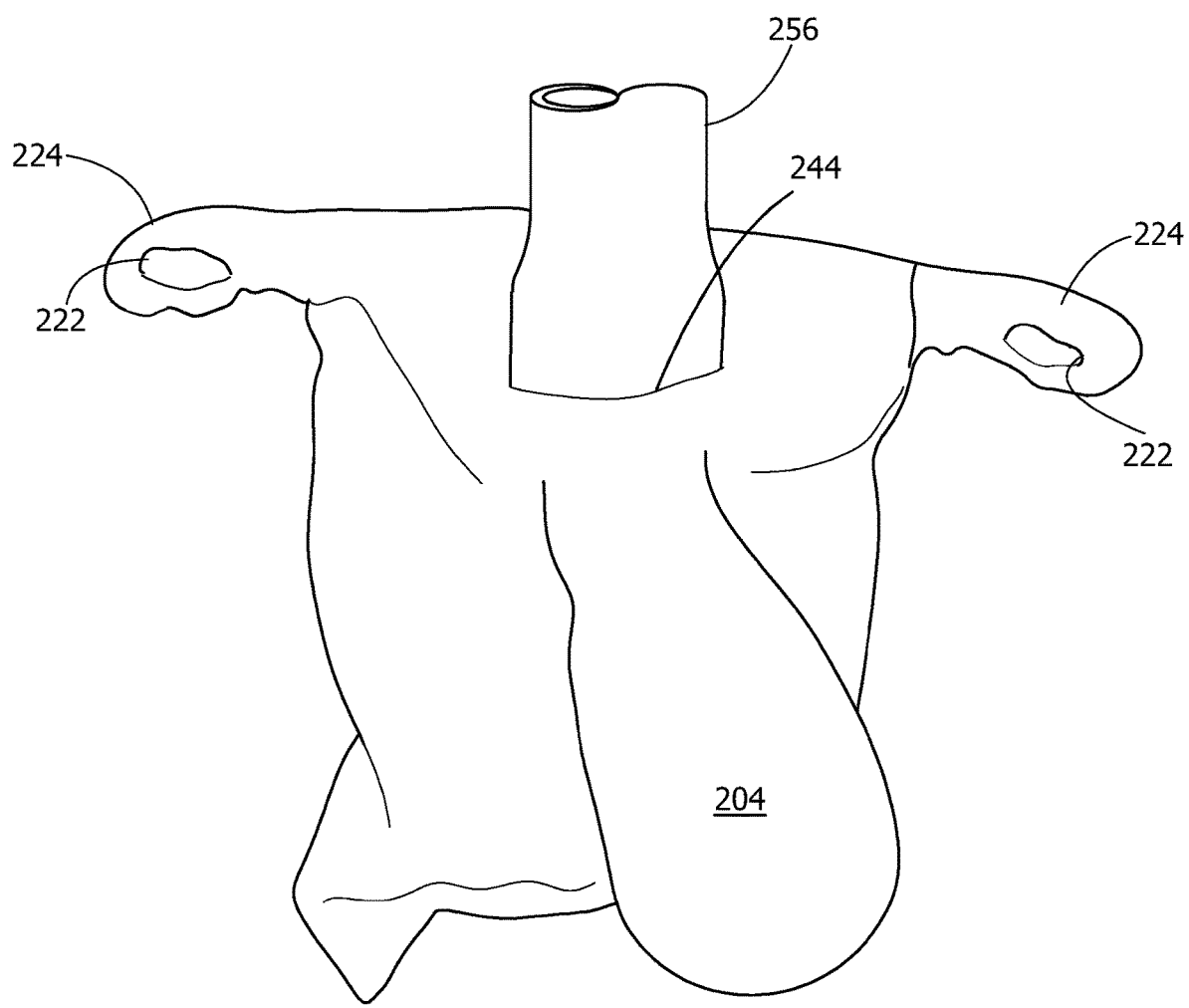

Once stethoscope head 12 has been inserted inside of pouch 206, user 28 releases tab 204. As shown in FIG. 30, open end 244 of pouch 206, while no longer in open position 250 (FIG. 29), is in a partially enlarged or extended condition, due to continued engagement of retainers 222 of support structures 224 with elongated members 214. As shown in FIG. 30A, upon retainers 222 being removed from tips 216 of elongated members 214, open end 244 will collapse around tubing 256, and the cover will similarly collapse around the head of the stethoscope.

Figure 33:
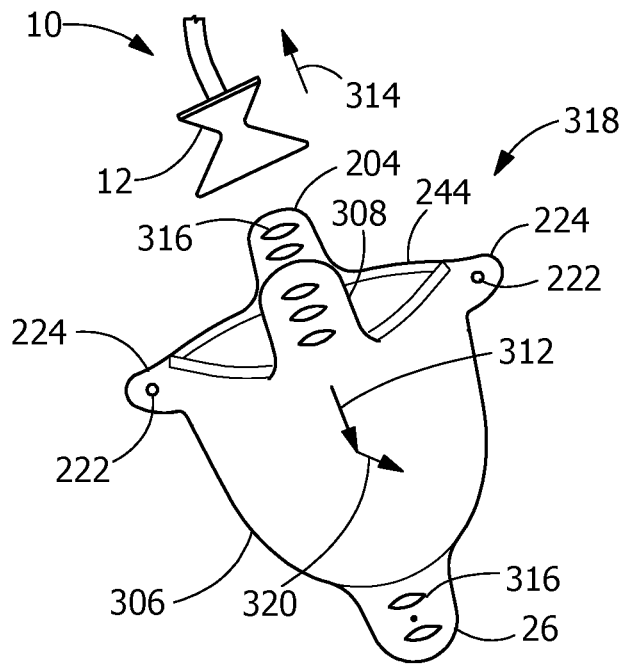
FIG. 33 is an oblique perspective view of an exemplary cover for covering a stethoscope head.

FIGS. 33-41 showing exemplary embodiments of pouches are now discussed. FIG. 33 shows a pouch 306 incorporating various features of different pouches previously discussed, including pouch 18 (FIG. 2), pouch 132 (FIG. 18), pouch 206 (FIG. 22) except as shown. For example, pouch 306 includes a tab 308 proximate open end 244 that is opposite tab 204, permitting removal of the stethoscope head from the pouch. That is, in response to a user (not shown) wearing stethoscope 10 (e.g., the headset of the stethoscope encircling the user's neck) with a stethoscope head 12 positioned interior or inside of pouch 306, in response to the user grasping tabs 204, and 308 and plot and simultaneously applying forces generally in a removal force direction 312 that is opposite a retention force direction 314 applied to the stethoscope headset by the user, the stethoscope head can be removed from pouch 306. In one embodiment, each removal force direction 312 includes opposed lateral force components 320 (only one lateral force component 320 as shown in FIG. 33) to help further increase the space between tabs 204, 308 to promote easier removal of the stethoscope head from pouch 306. In one embodiment, the user may grasp one of tabs 204, 308 and tab 26, simultaneously applying forces generally in a removal force direction 312 is opposite a retention force direction 314 applied to the stethoscope headset by the user for removing the stethoscope head can be removed from pouch 306. In one embodiment, the user may only grasp tab 26, simultaneously applying a force generally in a removal force direction 312 that is opposite a retention force direction 314 applied to the stethoscope headset by the user for removing the stethoscope head from pouch 306. In one embodiment, the user may only grasp tab 204 or tab 308, simultaneously applying forces generally in a removal force direction 312 that is opposite a retention force direction 314 applied to the stethoscope headset by the user, for removing the stethoscope head from pouch 306.

It is to be understood that different tab arrangements may be used with the pouch. For example, in one embodiment, only tabs 204, 308 are included. In one embodiment, only tabs 26, 204 are included. In one embodiment, only tabs 26, 308 are included. In one embodiment, only one of tab 204 or tab 308 is included.

Figure 34:
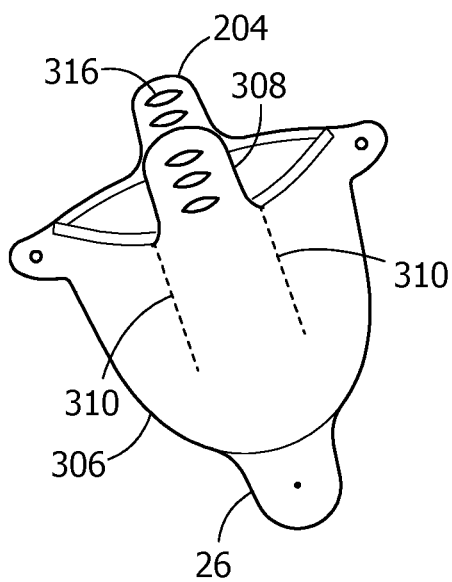
FIG. 34 is an oblique perspective view of an exemplary cover for covering a stethoscope head.

As further shown in FIG. 33, a plurality of grip enhancement features or retainers may be formed 316 on tabs 26, 204, 308. As shown in FIG. 34, at least one weakened region 310, such as a perforation, or areas of reduced thickness or combination thereof may be formed in pouch 306.

Figure 35:
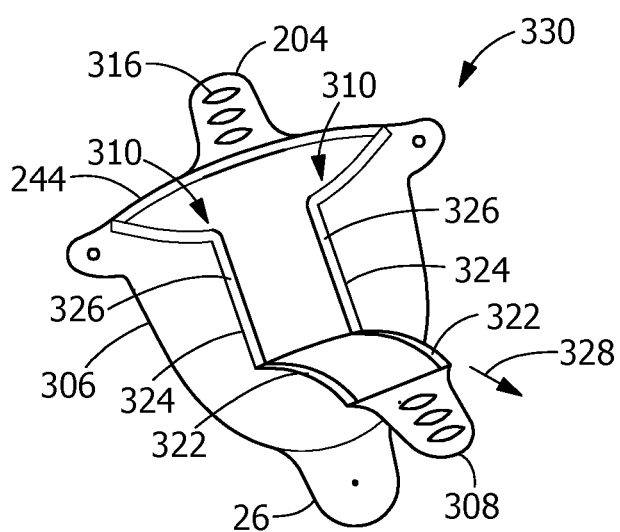
FIG. 35 is an oblique perspective view of the cover of FIG. 34 in an open position for removal of a stethoscope head.

As shown in FIG. 35, weakened regions 310 include at least one slit 324 formed in pouch 306 for separating tab 308 from pouch 306. Along each slit 324 an adhesive strip 322 extends along a periphery of tab 308, and corresponds to an adhesive retention strip 326 extending along a periphery of pouch 306. In one embodiment, the arrangement is reversed; that is, adhesive strip 322 extends along a periphery of pouch 306 and adhesive retention strip 326 extends along a periphery of tab 308. In one embodiment, the arrangement may be a combination of both; i.e., adhesive strip 322 extends along one periphery of tab 308, and adhesive retention strip 326 extends along the other periphery of tab 308 with the strips 322, 326 extending along the corresponding peripheries of pouch 306. Either prior to use of pouch 306, such as in a collapsed condition, or in a "ready to use" condition of pouch 306 with stethoscope head 12 (FIG. 33) positioned inside of pouch 306 by steps previously discussed, slit 324 is closed reinforced in a closed position as a result of adhesive strip 322 engaging adhesive retention strip 326. To permit removal of stethoscope head 12 (FIG. 33) from pouch 306, a user (not shown) grasps tab 308 and applies a separation force 328 in a direction away from pouch 306 sufficient for opening weakened regions 310, forming an open position 330 in pouch 306 by enlarging open end 244. In one embodiment, removal of stethoscope head 12 (FIG. 33) may be achieved with one hand (i.e., the user only grasping tab 308 and combination with application of separation force 328, opposite retention force direction 314 (FIG. 33) applied to the stethoscope headset by the user, application of the retention force direction 314 not requiring the user's hands. In one embodiment, removal of stethoscope head 12 (FIG. 33) may be achieved with both hands, such as by grasping tab 308 and one of tab 204 or tab 26 in a manner previously discussed.

Figure 36:
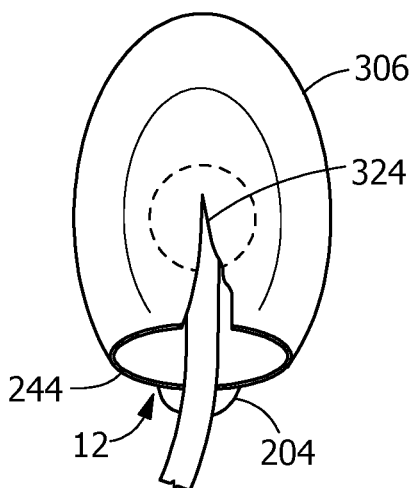
FIG. 36 is a front upper perspective view of an exemplary cover for covering a stethoscope head.

FIGS. 36-41 showing exemplary embodiments of pouch constructions utilizing slit 324 are now discussed. For example, as shown in FIG. 36, slit 324 is positioned by itself on one side of pouch 306, with tab 204 positioned on the opposite side of pouch 306, with removal of stethoscope head 12 from pouch 306 resulting from a sufficient removal force being applied to tab 204 to urge slit 324 to open, thereby enlarging open end 244 in a manner as previously discussed.

Figure 37:
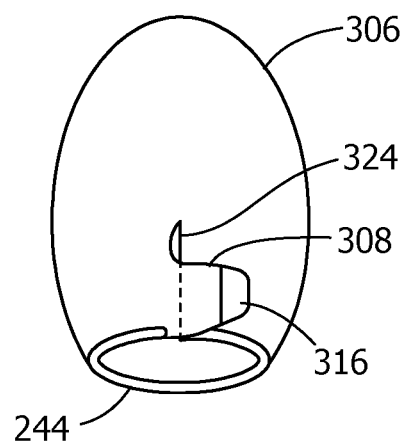
FIG. 37 is a front upper perspective view of an exemplary cover for covering a stethoscope head.
Figure 40:
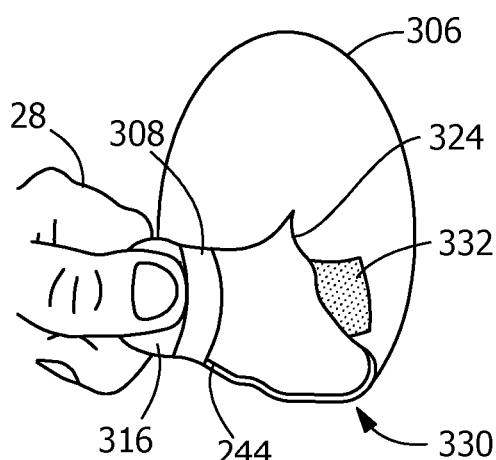
FIG. 40 is a front upper perspective view of the cover of FIG. 37 in an open position for receiving or removing a stethoscope head.

FIG. 37 shows tab 308 formed from the same material as pouch 306, and more specifically tab 308 being of one-piece or unitary construction with pouch 306, with tab 308 extending in a non-parallel direction with respect to slit 324, such as tab 308 being perpendicular to slit 324, although different orientations are contemplated by the present invention. FIG. 40 shows pouch 306 of FIG. 37 in an open position 330, with retainers 316, 332 of corresponding tab 308 and pouch 306 being separated from one another.

Figure 38:
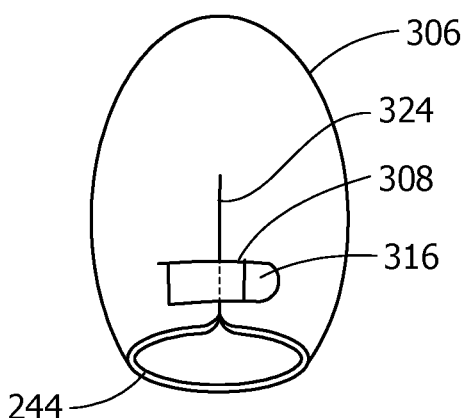
FIG. 38 is a front upper perspective view of an exemplary cover for covering a stethoscope head.
Figure 39:
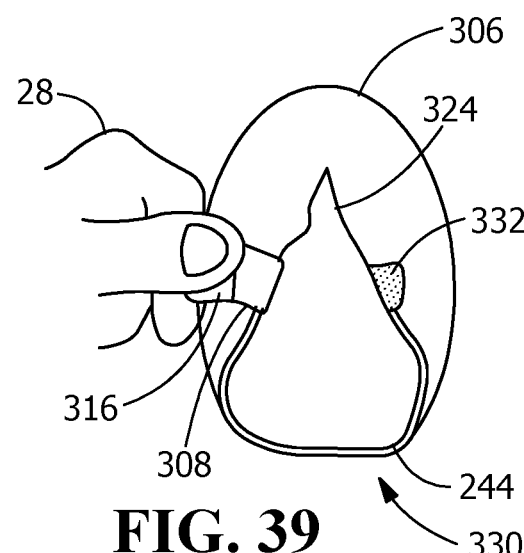
FIG. 39 is a front upper perspective view of the cover of FIG. 38 in an open position for receiving or removing a stethoscope head.

FIG. 38 shows tab 308 formed separately from pouch 306 and secured at one end to pouch 306, with tab 308 extending in a non-parallel direction with respect to slit 324, such as tab 308 being perpendicular to slit 324, although different orientations are contemplated by the present invention. FIG. 39 shows pouch 306 of FIG. 38 in an open position 330, with retainers 316, 332 of corresponding tab 308 and pouch 306 being separated from one another.

Figure 41:
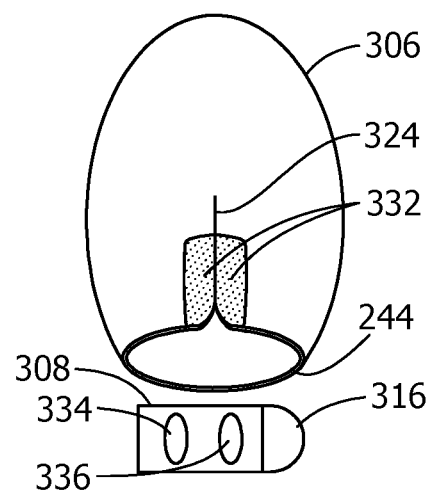
FIG. 41 is an exploded view of an exemplary cover for covering a stethoscope head.

FIG. 41 shows tab 308 formed separately from pouch 306 and removably securable by a retainer 334 at one end to pouch 306 to a corresponding retainer positioned along one side of slit 324, and with tab 308 being removably securable by a retainer 336 to a corresponding retainer positioned along the opposed side of slit 324. As shown, tab 308 extends in a non-parallel direction with respect to slit 324, such as tab 308 being perpendicular to slit 324, although different orientations are contemplated by the present invention.

The present invention has been described as a cover, dispenser and method for covering and uncovering a stethoscope. It will be understood that the above description is merely illustrative of the applications of the principles of the present invention, the scope of which is to be determined by the claims viewed in light of the specification. Other variants and modifications of the invention will be apparent to those of skill in the art.

What is claimed is:

1. A system for dispensing sterile covers for a stethoscope, comprising:
    a container including at least two elongated members positioned in the container and terminating at tips proximate one end of the container, wherein the at least two elongated members are arranged non-parallel to one another, wherein the at least two elongated members are rods, wherein the at least two elongated members extend from interior of the container through an opening in the one end of the container to outside of the container;
    a plurality of collapsed pouches positioned inside the container, each pouch having an open end and a closed end and a support structure positioned proximate the open end, the support structure having a pair of first retainers, each first retainer adapted to receive a corresponding elongated member of the at least two elongated members, the plurality of collapsed pouches being supported on the elongated members, each pouch comprising a tab positioned proximate the open end;
    the tab being arranged and disposed such that in response to the tab of the corresponding pouch positioned nearest to the tips of the at least two elongated members being grasped and pulled in a direction downwards along and away from the at least two elongated members, the open end forming a first open position defined by the pair of first retainers and the tab and for receiving a head of the stethoscope inside the corresponding pouch while the first retainers remain engaged with the at least two elongated members.

2. The system of claim 1, wherein the container includes a removable lid at the one end to expose the corresponding pouch positioned nearest to the tips for removal from the container.

3. The system of claim 1 further comprising a receptacle adapted to receive the container.

4. The system of claim 3 further comprising container indicia located on the container, wherein the receptacle includes slots for permitting viewing of the container indicia.

5. The system of claim 4, wherein the container indicia include product description information and product usage steps.

6. The system of claim 3, wherein the receptacle comprises a plurality of interconnected walls, the receptacle being adapted to support the container.

7. The system of claim 6, wherein one of the plurality of interconnected walls at a first end of the receptacle supports the one end of the container and includes an opening, the at least two elongated members extending through the opening for removal of the corresponding pouch positioned nearest to the tips through the opening at the first end of the receptacle.

* * * * *